United States Patent
Rowe et al.

(10) Patent No.: US 10,350,263 B2
(45) Date of Patent: Jul. 16, 2019

(54) COMPOUNDS AND METHODS FOR INCREASING HAIR GROWTH

(71) Applicant: The University of Kansas, Lawrence, KS (US)

(72) Inventors: Peter S. N. Rowe, Prairie Village, KS (US); Aline Martin, Miami, FL (US); Nicolae Valentin David, Miami, FL (US); M. Laird Forrest, Lawrence, KS (US); Kenneth Ryan Moulder, Lawrence, KS (US); Shuang Cai, Lawrence, KS (US); Daniel J. Aires, Prairie Village, KS (US)

(73) Assignee: The University of Kansas, Lawrence, KS (US)

(*) Notice: Subject to any disclaimer, the term of this patent is extended or adjusted under 35 U.S.C. 154(b) by 0 days.

(21) Appl. No.: 16/275,069

(22) Filed: Feb. 13, 2019

(65) Prior Publication Data

US 2019/0167757 A1 Jun. 6, 2019

Related U.S. Application Data

(62) Division of application No. 15/113,732, filed as application No. PCT/US2015/012691 on Jan. 23, 2015, now Pat. No. 10,213,479.

(60) Provisional application No. 61/930,749, filed on Jan. 23, 2014.

(51) Int. Cl.
| | |
|---|---|
| *A61K 38/00* | (2006.01) |
| *A61K 38/16* | (2006.01) |
| *A61K 8/64* | (2006.01) |
| *A61K 8/14* | (2006.01) |
| *A61K 47/10* | (2017.01) |
| *A61K 45/06* | (2006.01) |
| *A61K 31/58* | (2006.01) |
| *A61K 9/00* | (2006.01) |
| *A61K 9/127* | (2006.01) |
| *A61K 9/107* | (2006.01) |
| *A61Q 7/00* | (2006.01) |
| *A61K 31/506* | (2006.01) |
| *A61K 47/69* | (2017.01) |

(52) U.S. Cl.
CPC ............ *A61K 38/16* (2013.01); *A61K 8/14* (2013.01); *A61K 8/64* (2013.01); *A61K 9/0014* (2013.01); *A61K 9/1075* (2013.01); *A61K 9/127* (2013.01); *A61K 31/506* (2013.01); *A61K 31/58* (2013.01); *A61K 45/06* (2013.01); *A61K 47/10* (2013.01); *A61K 47/6911* (2017.08); *A61Q 7/00* (2013.01); *A61K 2800/412* (2013.01)

(58) Field of Classification Search
None
See application file for complete search history.

(56) References Cited

U.S. PATENT DOCUMENTS

| | | |
|---|---|---|
| 2007/0086972 A1 | 4/2007 | Birnbaum |
| 2010/0041773 A1 | 2/2010 | Peterson |
| 2010/0298365 A1 | 11/2010 | Malek |
| 2012/0071399 A1 | 3/2012 | Rabbani et al. |
| 2012/0258972 A1 | 10/2012 | Rafi et al. |

FOREIGN PATENT DOCUMENTS

WO 2008/033488 A2 3/2008

OTHER PUBLICATIONS

Atkins et al. Sclerostin is a Locally Acting Regulator of Late-Osteoblast/Preosteocyte Differentiation and Regulates Mineralization Through a MEPE-ASARM-Dependent Mechanism, Journal of Bone and Mineral Research, Jul. 2011, vol. 26, No. 7, pp. 1425, 1436, Figure 6.

Written Opinion of the International Searching Authority, as issued in connection with International Patent Application No. PCT/US2015/012691, dated Sep. 8, 2015, 8 pgs.

International Search Report, as issued in connection with International Patent Application No. PCT/US2015/012691, dated Sep. 8, 2015, 5 pgs.

David V, Martin AC, Hedge AM, Drezner MK, Rowe PS. ASARM peptides: PHEX-dependent & independent regulation of serum phosphate. Am J Physiol Renal Physiol. 2011;300(3):F783-91.

Atkins GJ, Rowe PS, Lim HP, Welldon KJ, Ormsby R, Wijenayaka AR, Zelenchuk L, Evdokiou A, Findlay DM. Sclerostin is a locally acting regulator of late-osteoblast/pre-osteocyte differentiation and regulates mineralization through a MEPE-ASARM dependent mechanism. J Bone Miner Res. 2011;26(7):1425-36.

Martin A, David V, Laurence JS, Schwarz PM, Lafer EM, Hedge AM, Rowe PS. Degradation of MEPE, DMP1, and release of Sibling ASARM-peptides (minhibins): ASARM-peptide(s) are directly responsible for defective mineralization in HYP. Endocrinology. 2008;149(4):1757-72.

David V, Martin A, Hedge AM, Rowe PS. Matrix extracellular phosphoglycoprotein (MEPE) is a new bone renal hormone and vascularization modulator. Endocrinology. 2009;150(9):4012-23.

(Continued)

*Primary Examiner* — Jeanette M Lieb
(74) *Attorney, Agent, or Firm* — Maschoff Brennan

(57) ABSTRACT

A method of promoting hair growth can include: a polypeptide having a sequence that has at least 75% complementarity to or at least 75% identical to SPR4; and topically administering the polypeptide to a subject. This can include putting or causing the polypeptide to be in the skin, such as in any dermal layer. In one aspect, the method can include administering the composition topically so as to administer the polypeptide to the subject. In one aspect, the method can include administering the polypeptide to skin of the subject. In one aspect, the method can include administering the polypeptide to a hair follicle of the subject. In one aspect, the method can include administering the polypeptide to a bald spot of the subject.

20 Claims, 17 Drawing Sheets

Specification includes a Sequence Listing.

(56) References Cited

OTHER PUBLICATIONS

Rowe PS, Matsumoto N, JO OD, Shin RN, Oconner J, Roudier MP, Bain S, Liu S, Harrison J, Yanagawa N. Correction of the mineralization defect in hyp mice treated with protease inhibitors CA074 and pepstatin. Bone. 2006;39(4):773-86.

Rowe PSN, Garret IR, Schwarz PM, Carnes DL, Lafer EM, Mundy GR, Gutierrez GE. Surface Plasmon Resonance (SPR) confirms MEPE binds to PHEX via the MEPE-ASARM-motif: A model for impaired mineralization in X-linked rickets (HYP). Bone. 2005;36(1):33-46.

Rowe PS, Kumagai Y, Gutierrez G, Garret IR, Blacher R, Rosen D, Cundy J, Navvab S, Chen D, Drezner MK, Uarles LD, Mundy GR. MEPE has the properties of an osteoblastic phosphatonin and minhibin. Bone. 2004;34(2)303-19. PMCID: 3357088.

Yuan B, Takaiwa M, Clemens TL, Feng JQ, Kumar R, Rowe PS, Xie Y, Drezner MK. Aberrant Phex function in osteoblasts and osteocytes alone underlies murine X-linked hypophosphatemia. J Clin Invest. 2008;118 (2):722-34.

Bresler D, Bruder J, Mohnike KL, Fraser D, Rowe PSN. Serum MEPE-ASARM-peptides are elevated in X-linked rickets (HYP): implications for phosphaturia and rickets. J Endocrinology. 2004;183:R1-9.

Pfaffl MW. A new mathematical model for relative quantification in real-time RT-PCR. Nucleic Acids Res. 2001;29 (9):e45. PMCID: 55695.

Gluhak-Heinrich J, Ye L, Bonewald LF, Feng JQ, Macdougall M, Harris SE, Pavlin D. Mechanical loading stimulates dentin matrix protein 1 (DMP1) expression in osteocytes in vivo. J Bone Miner Res. 2003;18 (5):807-17.

Verma DD, Fahr A. Synergistic penetration enhancement effect of ethanol and phospholipids on the topical delivery of cyclosporin A. Journal of controlled release : official journal of the Controlled Release Society. 2004;97(1):55-66.

Crabtree JS, Kilbourne EJ, Peano BJ, Chippari S, Kenney T, Mcnally C, Wang W, Harris HA, Winneker RC, Nagpal S, Thompson CC. 2010 A mouse model of androgenetic alopecia. Endocrinology 151 (5):2373-80.

Park HJ, Zhang N, Park DK. 2011 Topical application of Polygonum multiflorum extract induces hair growth of resting hair follicles through upregulating Shh and beta-catenin expression in C57BL16 mice. J Ethnopharmacol 135 (2):369-75.

Park WS, Lee CH, Lee BG, Chang IS. 2003 The extract of Thujae occidentalis semen inhibited 5alphareductase and androchronogenetic alopecia of B6CBAF1/j hybrid mouse. J Dermatol Sci 31(2):91-8.

Matias JR, Malloy V, Orentreich N. 1989 Animal models of androgen-dependent disorders of the pilosebaceous apparatus. 1. The androchronogenetic alopecia (AGA) mouse as a model for malepattem baldness. Arch Dermatol Res 281(4)247-53.

Matias JR, Orentreich N. 1988 The effect of testosterone, cyproterone acetate, and minoxidil on hair loss in the androchronogenetic alopecia mouse. Clin Dermatol 6(4):169-76.

Millar, S. E., et al., "WnNT Signaling in the Control of Hair Growth and Structure," Developmental Biology, 207, pp. 133-149 (1999).

Faber-Barata, J., Sola-Penna, M., "Opposing effects of two osmolytes—trehalose and glycerol —on the thermal inactivation of rabbit muscle 6-phosphofructo-1-kinase," Molecular and Cellular Biochemisty, 269, pp. 203-207 (2005).

Fluorescent labeled SPR4 peptide: Dermal topical application.

ROW A.

40X magnification

ROW B.

Subcutaneous Fat Cell Layer

ROW C.

60X magnification

5α-DHT mice: Increase weight, BMD and Lean/Fat mass
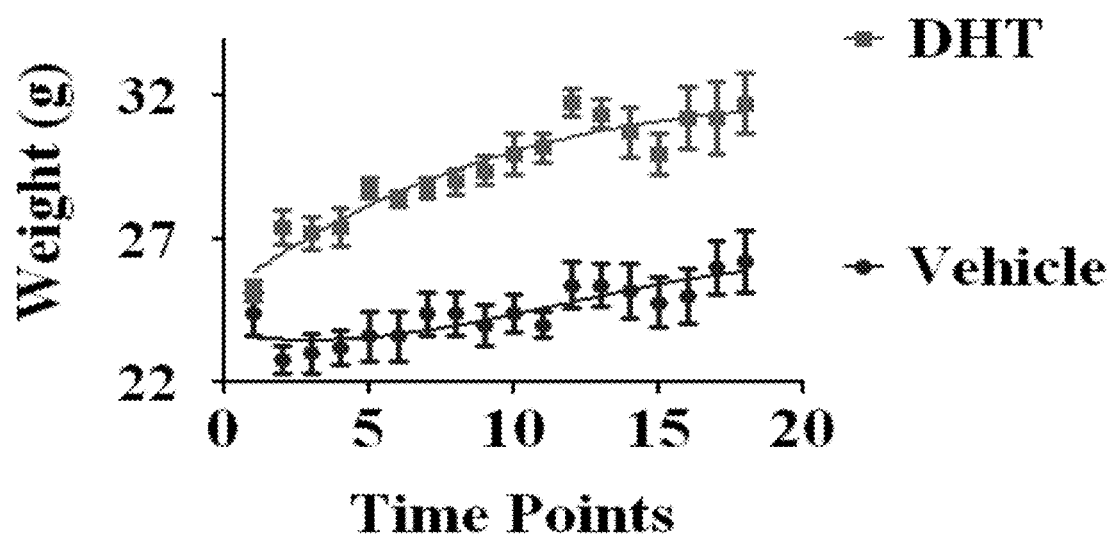
Fig. 8A
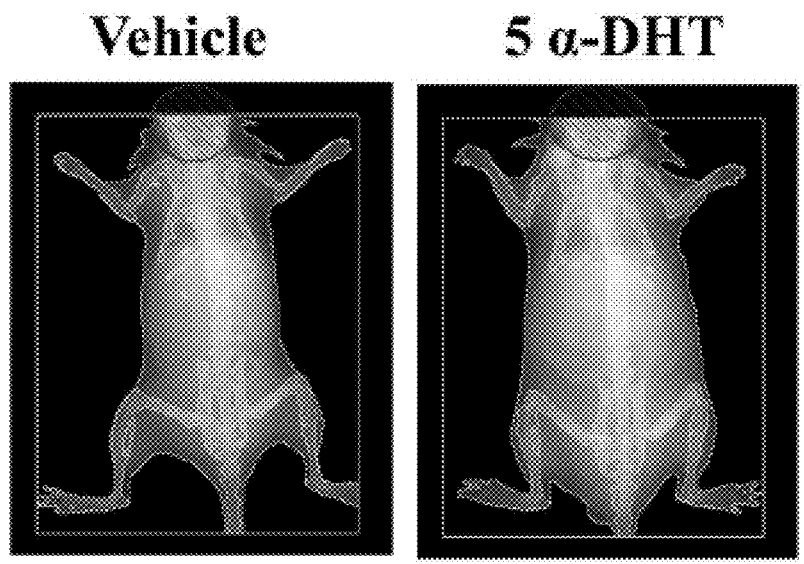
Fig. 8B  Dual Energy X-Ray Absorptiometry (DEXA)

| d(nm) | G(d) | C(d) | d(nm) | G(d) | C(d) | d(nm) | G(d) | C(d) |
|---|---|---|---|---|---|---|---|---|
| 340.4 | 26 | 5 | 375.6 | 97 | 40 | 401.0 | 80 | 75 |
| 349.2 | 44 | 10 | 379.0 | 99 | 45 | 405.8 | 70 | 80 |
| 355.4 | 58 | 15 | 382.3 | 100 | 50 | 411.4 | 58 | 85 |
| 360.3 | 70 | 20 | 385.8 | 99 | 55 | 418.6 | 44 | 90 |
| 364.6 | 80 | 25 | 389.2 | 97 | 60 | 429.4 | 26 | 95 |
| 368.4 | 87 | 30 | 392.9 | 93 | 65 | | | |
| 372.1 | 93 | 35 | 396.8 | 87 | 70 | | | |

Median Diam. 382.3 nm
Mean Diam. 383.3 nm
Polydispersity 0.005
GSD 1.073

Zeta: -38.2

| Median Diam. | 152.8 nm |
| Mean Diam. | 157.2 nm |
| Polydispersity | 0.059 |
| GSD | 1.270 |

Zeta: -37.9

| d(nm) | G(d) | C(d) | d(nm) | G(d) | C(d) | d(nm) | G(d) | C(d) |
|---|---|---|---|---|---|---|---|---|
| 103.1 | 26 | 5 | 143.8 | 97 | 40 | 179.5 | 80 | 75 |
| 112.5 | 44 | 10 | 148.3 | 99 | 45 | 186.9 | 70 | 80 |
| 119.3 | 58 | 15 | 152.8 | 100 | 50 | 195.7 | 58 | 85 |
| 124.9 | 70 | 20 | 157.5 | 99 | 55 | 207.6 | 44 | 90 |
| 130.1 | 80 | 25 | 162.3 | 97 | 60 | 226.4 | 26 | 95 |
| 134.8 | 87 | 30 | 167.5 | 93 | 65 | | | |
| 139.4 | 93 | 35 | 173.2 | 87 | 70 | | | |

SEQUENCE LISTING

```
<160> NUMBER OF SEQ ID NOS: 1

<210> SEQ ID NO 1
<211> LENGTH: 46
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 1

Thr Val Asn Ala Phe Tyr Ser Ala Ser Thr Asn Tyr Pro Arg Ser Leu
1               5                   10                  15

Ser Tyr Gly Ala Ile Gly Val Ile Val Gly His Glu Phe Thr His Gly
            20                  25                  30

Phe Asp Asn Asn Gly Arg Gly Glu Asn Ile Ala Asp Asn Gly
        35                  40                  45
```

COMPOUNDS AND METHODS FOR INCREASING HAIR GROWTH

CROSS-REFERENCE

This patent application is a divisional application of U.S. application Ser. No. 15/113,732 with a section 371 filing date of Jul. 2, 2016 and is now U.S. Pat. No. 10,213,489, which is a 371 nationalization of PCT No. PCT/US2015/012691 filed Jan. 23, 2015, which claims priority to U.S. Provisional Application No. 61/930,749 filed Jan. 23, 2014, which applications are incorporated herein by specific reference in their entirety.

GOVERNMENT RIGHTS

This invention was made with government support under AR051598 and CA173292 awarded by the National Institutes of Health. The government has certain rights in the invention.

BACKGROUND

In our recent studies we described a bio-engineered, 4.2 kDa synthetic PHEX-peptide (i.e., SPR4) also referred to as murikal that specifically binds and neutralizes ASARM-peptides. The SPR4 peptide also corrects the mineralization defect in vitro and in vivo and has positive effects on bone regulatory markers. These discoveries (ASARM and SPR4-peptides) have helped provide new strategies to treat select hypophosphatemic bone-mineralization disorders (HYP, ADHR, ARHR, osteoporosis and TIO) and manage hyperphosphatemia in CKD-MBD, ESRD. SPR4-peptide also improves and corrects energy metabolism in healthy mice and mice with hypophosphatemic bone-mineral loss disorders (HYP mice) respectively. The improvements in energy metabolism may have therapeutic utility for osteoporosis, obesity, metabolic syndrome and diabetes. Also, SPR4-peptide in conjunction with a replete phosphate diet may be used to treat inherited hypophosphatemic bone-mineral loss disorders (X-linked rickets (HYP) and autosomal forms of rickets (recessive and dominant)).

BRIEF DESCRIPTION OF THE FIGURES

The foregoing and following information as well as other features of this disclosure will become more fully apparent from the following description and appended claims, taken in conjunction with the accompanying drawings. Understanding that these drawings depict only several embodiments in accordance with the disclosure and are, therefore, not to be considered limiting of its scope, the disclosure will be described with additional specificity and detail through use of the accompanying drawings, in which:

FIGS. 8A-8B includes DEXA analysis pictures of representative Vehicle and 5α-DHT male castrated mice showing increased bone and lean mass with treated mice.

DETAILED DESCRIPTION

Figure 1:
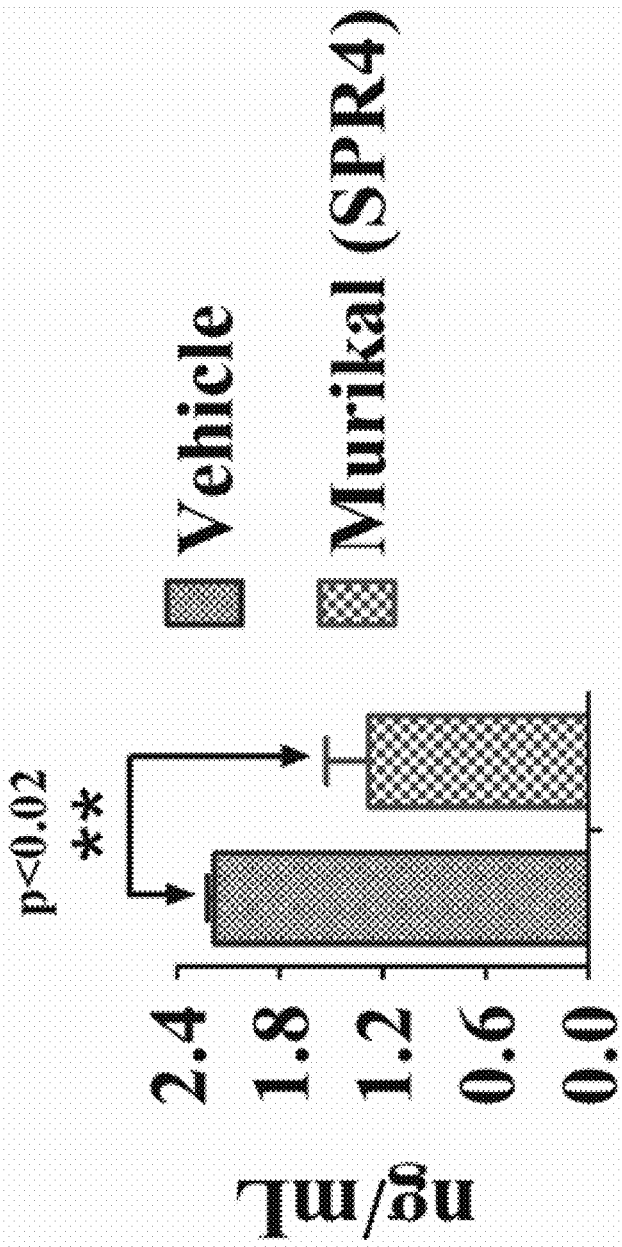
FIG. 1 includes data that shows suppression of circulating sclerostin in wild type mice infused with SPR4 using osmotic pump infusion.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented herein. It will be readily understood that the aspects of the present disclosure, as generally described herein, and illustrated in the figures, can be arranged, substituted, combined, separated, and designed in a wide variety of different configurations, all of which are explicitly contemplated herein. Generally, the present technology includes a pharmaceutical preparation that can increase hair growth when topically applied to the skin. More specifically, this technology includes a 4.2 kDa peptide (i.e., SPR4) in a lipid or polymer-based formulation configured for transdermal delivery that dramatically increases hair growth when topically applied to skin. Also, the present technology relates to use of the novel peptide (i.e., SPR4) that is bioengineered and modeled from the catalytic binding site of "Phosphate Regulating Gene with Endopeptidase Homologies" (PHEX) and the associated molecular pathways that stimulate accelerated hair growth.

The SPR4 can increase hair growth when applied to skin. Proof of increased hair growth was observed in mice, and it is expected that such increased hair growth will occur in all mammals, and be useful for humans and other mammals to have increased hair growth. The peptide can be used to reduce or treat or prevent baldness, such as pattern baldness, male pattern baldness, or other types of baldness. As such, the peptide can be applied to skin, such as bald skin or skin under hair. The peptide can be applied to skin that has hair in humans that do not want to lose their hair, and thereby the peptide can be used for hair maintenance. As such, the peptide can be used to increase the duration of having hair and inhibiting the onset of baldness. The baldness to be improved by hair growth induced by the peptide can be natural baldness or induced baldness, such as chemotherapy, radiation, or other that causes baldness. The peptide can increase and induce new hair follicle growth, such as in bald spots or regions that have thin hair or even regions that have thick hair. The peptide can be applied topically alone or in a pharmaceutical composition. The composition can be configured for transdermal delivery of the peptide, and thereby can include penetration or permeation enhancers, which are well known in the pharmaceutical arts. The composition having the peptide can be applied to a bald spot or other skin location in a lotion or gel and allowed to absorb into the skin. Also, the composition can be a shampoo that is applied to a bald head and/or hair so that the bald spots or thin hair areas or other skin areas can have enhanced hair growth, where the shampoo can be allowed to set for some period of time to allow transdermal delivery.

In one aspect, the delivery of the peptide may not be true transdermal delivery because the peptide only needs to enter into the skin for functionality. As such, the delivery may be considered to be dermal delivery or topical delivery or skin delivery; however, transdermal delivery is allowable. However, transdermal delivery agents, such as permeation or penetration enhancers that enhance entry of the peptide into skin can be used as a carrier for the peptide.

The peptide sequence of SPR4 is: NH2 TVNAFYSAST-NYPRSLSYGAIGVIVGHEFTHGFDNNGRGENIADNG-OH (SEQ ID NO: 1). This peptide may be used as shown, or it may be linked on the C-terminal end and/or N-terminal end to other peptides or chemical moieties. Peptide purity was greater than 90% via HPLC, ion-exchange and also mass spectrometry.

In one aspect, the peptide can be applied in a combination cancer therapy and baldness therapy. This can inhibit cancer and promote hair growth at the same time. This may be helpful for some skin cancers on bald spots, where the cancer and baldness can be simultaneously treated. For example, a cancer patient with hair loss can be administered the peptide for treating the cancer and to increase hair growth, such as when chemo or radiation has resulted in hair loss.

The peptide can be delivered by any mechanism or system that places the peptide in the skin and/or follicle and/or near the skin and/or follicle. The delivery can be by injection into the skin or across the skin. The injection can be a bolus or continuous or sustained. The delivery can be by topical application. The administration can be one time or repeated in an administration regimen. The administration can be topical or dermal or transdermal. The administration can be local or localized. The administration can be by a depot of degradable material (e.g., polymer) having the peptide so that degradation releases the peptide. The administration may also be systemic, where oral or i.v. administration may be possible.

SPR4 and related peptides directly regulate the Wnt/β-catenin canonical pathway and several genes important for hair growth. Specifically the current technology relates to the discovery that SPR4 can topically induce and accelerate hair growth and maintain an extended anagen phase when applied to the skin in a suitable formulation in the presence of low concentrations of $ZnCl_2$. Expression and stability of β-catenin is influenced by binding of Wnt to its cell-surface receptors (e.g., Frizzled or LRPS/6). The binding of Wnt to its co-receptors suppresses GSK kinase, an enzyme that when active phosphorylates active β-catenin (PO4-β-catenin). Phosphorylated β-catenin-PO4 is then targeted for ubiquitinylation and proteosomal degradation. Active unphosphorylated β-catenin travels to the nucleus where it binds to specific promoters and transcriptionally regulates target genes. In cells deplete of β-catenin due to reduced Wnt signaling, the transcriptional regulation of target genes is switched off. These target genes include those important for the anagen-phase of hair growth. Of relevance to the current technology, individuals with adrogenetic alopecia (or male pattern baldness), have increased levels of 5-α-reductase (5-αR). This enzyme (5-αR) converts testosterone to dehydro-testosterone (DHT) and DHT binds with specificity to the androgen receptor (AR). The DHT androgen-receptor complex (DHT-AR) then binds with high affinity and specificity to active β-catenin, and this has the effect of depleting endogenous levels of this important transcriptional regulator (β-catenin). This in turn results in a reduced anagen phase of the hair cycle and consequential hair thinning in those males and females with high levels of 5-αR. Application of SPR4 suppresses sclerostin expression and production resulting in increased Wnt signaling and increased active β-catenin. The increased β-catenin is then able to compensate for the DHT-AR mediated sequestration of β-catenin molecules and this restores the transcriptional activation of hair genes. This in turn induces hair growth and lengthens the anagen phase that then cures the baldness in afflicted individuals. Thus, the polypeptide can formulated for topical administration on the skin to maintain and/or promote hair growth, such as in a lipid emulsion, liposome or polymer particle for absorption into the skin and follicles.

Figure 2:
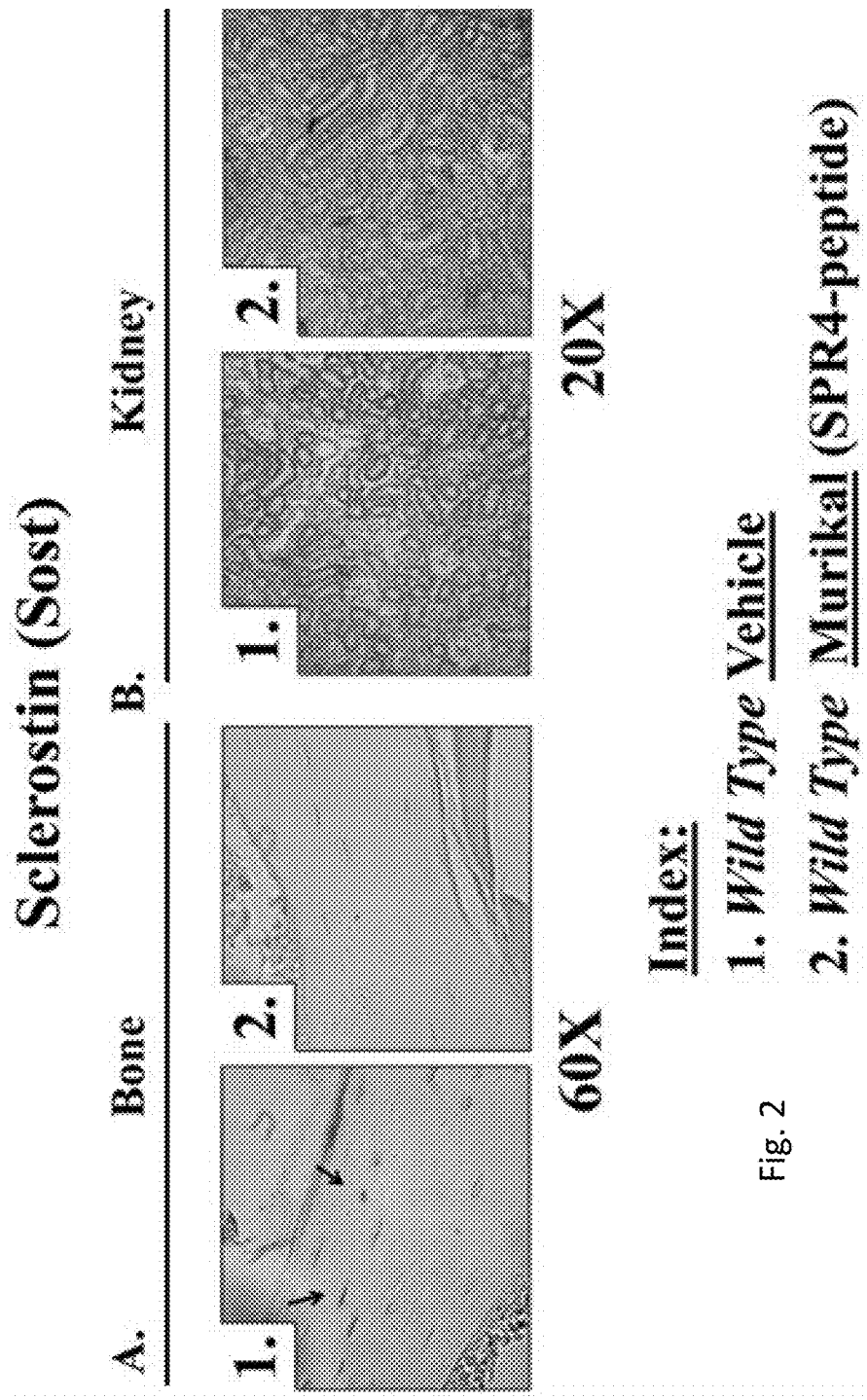
FIG. 2 include data that shows suppression of sclerostin in wild type mice cortical bone (femurs) as measured using immunohistochemistry (IHC) following infusion of SPR4 (SPR4-peptide). SPR4 and vehicle were infused using osmotic pumps as discussed.
Figure 3:
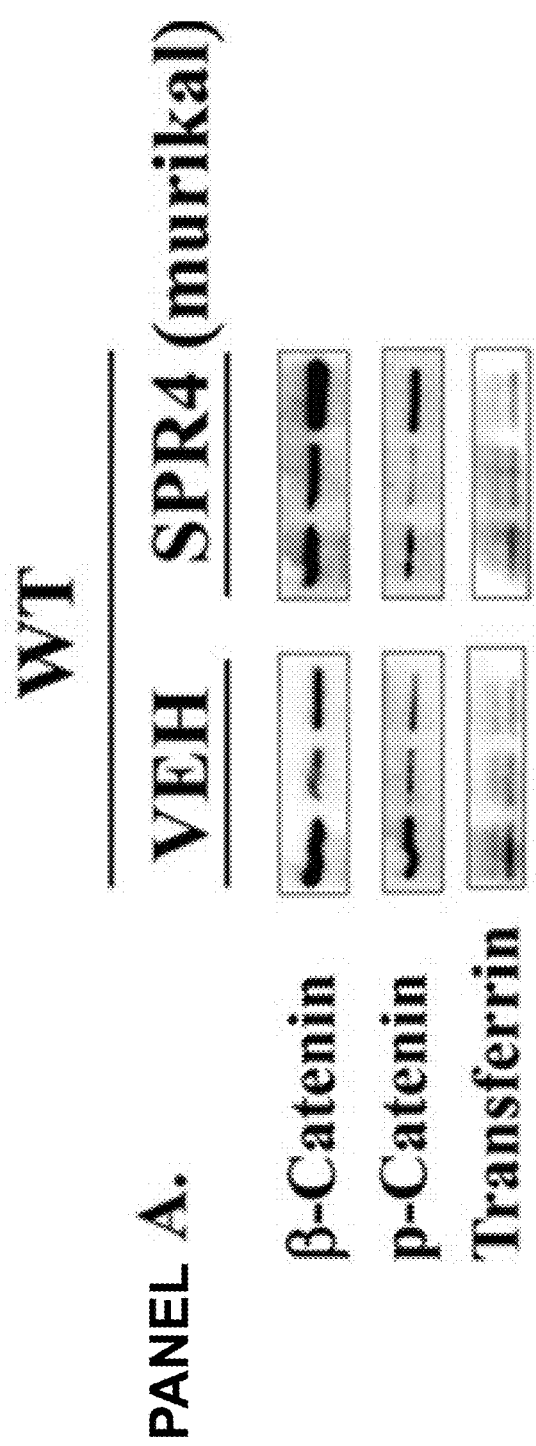
FIG. 3 shows increased active β-catenin protein-expression in wild type mice cortical bone (femurs) as measured by western-blotting following infusion of SPR4. SPR4 and vehicle.

SPR4 can mediate hair growth induction by positively affecting hair pattern baldness genes. Specifically, the effects of SPR4 can mediate correction of androgen dysregulation of the Wnt-β-catenin signaling pathway in dermal papilla cells from an androgenic alopecia (AGA) or male pattern baldness scalp. It was found that Wnt signals derived from undifferentiated matrix cells that give rise to the hair shaft precursor cells activate the Frizzled receptor (Frz) and LPRP5/6 co-receptor complex that in turn inactivates glycogen synthase kinase 3β (GSK-3β). When activated, GSK-3β kinase phosphorylates β-catenin (β-catenin-PO4) and this targets the molecule for ubiquitinylation and targeted proteosomal degradation. Wnt mediated inactivation of GSK-3β results in accumulation of active β-catenin that then translocates to the nucleus and cooperates with Tcf/Lef transcription factors to induce gene expression required for hair growth. However, in AGA testosterone (T) is efficiently converted to dehydrotestosterone (DHT) due to elevated levels of 5α-reductase, resulting in high levels of DHT and androgen-receptor (AR) that favor AR-β-catenin interactions. The AR-β-catenin interactions block β-catenin mediated gene expression. SPR4 peptide circumvents this process by suppressing sclerostin expression (e. g., a negative regulator of active β-catenin production). Sclerostin (SOST) suppresses active β-catenin levels by preventing LRPS/6 binding to Frizzled on the plasma membrane. The SOST inhibition of LRPS/6 binding to Frizzled in turn results in up regulation of GSK3β kinase that then phosphorylates β-catenin resulting in targeted ubiquitinylation and proteosomal degradation. Thus, the SPR4 mediated suppression of SOST and consequential increased β-catenin levels dynamically compensates for the increased DHT-AR receptor complex sequestration of free β-catenin. This in turn restores gene transcription and normal hair growth in individuals with hair pattern baldness. FIGS. 1, 2 and 3 show changes that lead to suppression of circulating sclerostin and increased active β-catenin in wild type mice infused with SPR4 using osmotic pump infusion.

The positive effects of systemic application of SPR4 on bone are mediated in part by suppression of Sclerostin (SOST), an inhibitor of the Wnt β-catenin canonical pathway. Specifically, SPR4 mediated inhibition of sclerostin induces active β-catenin that in turn has an anabolic effect on bone.

Of relevance to the present technology the Wnt/b-catenin canonical pathway plays a major role in regulating hair growth. Specifically, the present technology is directed to compositions and methods for promoting hair growth in individuals with androgenic alopecia (AGA) and also other hair baldness conditions by targeting a specific event in the Wnt/β-catenin canonical-pathway. In particular, a novel SOST-inhibitor peptide SPR4 and related compounds are provided. Local application of SPR4 and related peptides to the scalp and skin accelerates and sustains hair growth by lengthening the anagen phase and inducing β-catenin expression.

The SPR4 peptide and topical formulation overcomes delivery and administration and regimen issues. Previously, a primary issue with the formulation and subsequent treatment using non-small molecule drugs, such as peptides and macromolecules, has been the very poor biological absorption by routes other than intravenous, subcutaneous, and intramuscular. Previous treatments that may be self-administered by the patient on a periodic basis, such as several times a week, daily or more frequently, are inconvenient and difficult to administer by these routes. In addition, most parenteral routes result in systemic absorption and distribution, which can result in both sub-therapeutic drug levels at the intended site (e.g. the follicles or the dermis for a hair growth enhancing product) and non-specific drug actions in other tissues. Thus, the topical compositions with SPR4 offer an advantage.

Topical delivery is the preferred method of treatment with a SPR4 peptide hair growth enhancer since these formulations are convenient for the patient to apply and application can be limited to the areas where enhanced hair is desired. Thus, this technology is a non-irritating formulation that provides delivery of the polypeptide into the hair follicles and the dermis. Also, the formulation controls absorption into the dermis to limit the potential for systemic absorption via the lymph and hematological system, which can lead to dilution of the drug in the intended treatment area and the potential for exposing non-intended tissues to the drug.

The SPR4 hair enhancing products can be typically applied periodically, from several times a week, daily, to several times a day, and the application is often to public areas of the body, hence the formulation should be non-irritating and not cause discoloration of the skin. Lipid and polymeric formulations as described in this technology can deliver therapeutic levels of the SPR4 peptide into the hair follicles, while limiting dermal absorption, and not causing significant irritation or discoloration of the skin.

Peptide loaded liposomes were created using L-α-phosphatidylcholine (10 w/v %), ethanol (4.3 v/v %) and SPR4 (0.099% w/v). The ethanolic lipid mixture was vortexed for 5 minutes and sonicated until fully dissolved. SPR4 in PBS was then added while stirring. PBS was then added dropwise while stirring until the final concentration was reached. Loading degree of SPR4 within the liposome was determined using EZStart 7.4 software and a Shimadzu 2010CHT system with a TSKgel ODB 10 oz column (4.6 mm ID×25 cm, 5 μm) using ddH2O w/0.002% TFA and ACN w/0.002% TFA (1 ml/min). Organic solvent concentration within the method; 10% 0-5 minutes, linear increase to 90% 5-10 minutes, 90% 10-15 minutes, linear decrease to 10% 15-15.1 minutes and 10% 15.1-20 minutes. Retention time of the SPR4 peptide was found to be 10.35 minutes. Loading degree of most recent formulation method found to be 41.35% (w/w).

The loaded liposomes can be included in a micro or nano emulsion. The liposomes can be considered to be a pharmaceutical carrier. The micro or nano emulsions can be considered to be pharmaceutical carriers for the liposomes.

In one embodiment, a topical composition can include: a pharmaceutical carrier configured for topical application to a subject; and a polypeptide in the pharmaceutical carrier and having a sequence that has at least 75% complementarity to or at least 75% identical to SPR4, wherein SPR4 is: TVNAFYSASTNYPRSLSYGAIGVIVGHEFTH-GFDNNGRGENIADNG (SEQ ID NO: 1). In one aspect, the polypeptide has at least 80% complementarity to or is at least 80% identical to SPR4. In one aspect, the polypeptide has at least 90% complementarity to or is at least 90% identical to SPR4. In one aspect, the polypeptide has at least 95% complementarity to or is at least 95% identical to SPR4. In one aspect, the polypeptide has at least 99% complementarity to or is at least 99% identical to SPR4. In one aspect, the polypeptide has 100% complementarity to or is 100% identical to SPR4.

In one embodiment, the polypeptide is included in a fusion polypeptide with second polypeptide. The second polypeptide can be any polypeptide, which can be on the N- or C-terminus. The polypeptide can provide beneficial properties, such as water solubility, receptor targeting, endosomal escape, hair growth promotion, cell growth promotion, or any other benefit. In one aspect, the endosomal disrupting polypeptide includes PC4 or derivative thereof.

In one embodiment, the polypeptide is present in an amount sufficient to increase hair growth in a subject upon topical application to the subject. In one aspect, the polypeptide is present in an amount sufficient to increase hair follicle growth/development in a subject upon topical application to the subject.

In one embodiment, the polypeptide is dissolved in the carrier. In one aspect, the carrier includes one or more of cetearyl alcohol, cetearyl glucoside, squalane, isopropyl palmate, octyldodecaonol, phenoxyethanol, methylparaben, etheylparaben, butylparaben, propylparaben, isobutylparaben, glycerin, butylene glycol, sodium acrylate, acryloyldimethyl taurate, isohexadecane, polysorbate, glyceryl stearate, dicaprylyl ether, alkyl benzoate, isononyl isononanoate, methylpropanediol, tetrasodium EDTA, iodoproynyl butylcarbamate, triethanolamine, ketoconazole, serenoa serrulata extract, emu oil, niacin vitamin B3, caffeine, pyridoxine, L-pathenol, linolenic acid, simmondsia chinesis seed oil, zinc oxide, lecithin, $ZnCl_2$, L-α-phosphatidylcholine, ethanol, PBS, phospholipids, fatty acids, tocopherol, and derivatives thereof and equivalents thereof. In one aspect, the polypeptide is contained in a liposome or microsphere or polymer particle or lipid emulsion or combination thereof, and such can be included in a carrier.

In one embodiment, the composition can also include an active hair growth agent. In one aspect, the active hair growth agent is selected from minoxidil and finasteride.

In one embodiment, the composition promotes an anagen hair growth phase. In one embodiment, the composition promotes a catagen hair growth phase. In one embodiment, the composition promotes a telogen hair growth phase. In one embodiment, it can be any one or more or all three of these hair growth phases.

In one embodiment, the composition treats alopecia and related symptoms and related methods thereof. This can include administering a sufficient amount for any or the methods or treatments or hair growth maintenance as described herein. People with full thick hair can use in methods to maintain the full thick hair.

A method of promoting hair growth can include: a polypeptide having a sequence that has at least 75% complementarity to or at least 75% identical to SPR4; and topically administering the polypeptide to a subject. This can include putting or causing the polypeptide to be in the skin, such as in any dermal layer. In one aspect, the method can include administering the composition topically so as to administer the polypeptide to the subject. In one aspect, the method can include administering the polypeptide to skin of the subject. In one aspect, the method can include administering the polypeptide to a hair follicle of the subject. In one aspect, the method can include administering the polypeptide to a bald spot of the subject. In one aspect, the method can include administering the polypeptide so as to modulate the Wnt/beta-catenin canonical pathway. In one aspect, the method can include administering the polypeptide to regulate one or more genes involved in hair growth. In one aspect, the method can include administering the polypeptide so as to accelerate hair growth. In one aspect, the method can include administering the polypeptide so as to lengthen the anagen phase. In one aspect, the method can include administering the polypeptide so as to reduce 5-alpha-reductase. In one aspect, the method can include administering the polypeptide so as to suppress sclerostin. In one aspect, the method can include administering the polypeptide so as to increase Wnt signaling. In one aspect, the method can include administering the polypeptide so as to increase active beta-catenin. In one aspect, the method can include administering the polypeptide in an amount to treat alopecia and/or related syndromes. In one aspect, the method can include administering the polypeptide in an amount to lengthen the anagen phase. In one aspect, the method can include administering the polypeptide in an amount to increase hair growth on a bald spot. In one aspect, the method can include administering the polypeptide in an amount to increase hair follicle growth. In one aspect, the method can include administering the polypeptide in an amount to increase hair growth compared to when the polypeptide is not administered. Accordingly, castrated B6CBAF1/J hybrid male mice treated with 5-αDHT infused pellets provide for the first time a powerful and new model for the study of AGA in mice. In one aspect, the SPR4 peptide can be formulated into a gel. The gel may or may not include the liposome or other particle having the SPR4 encapsulated therein.

In one aspect, delivery of the SPR4 peptide to skin can be via microneedle application. A derma-roller application system that has microneedle disk rollers (high quality medical grade steel) can deliver the SPR4 peptide. This system is used in patients for the dermal application (cosmetic and medical) of medications and cosmetic pharmaceuticals in humans. The system is highly effective, painless and non-invasive (no blood released). The micro-roller provides a direct way of introducing SPR4 through the dermis into the circulation or into the sub-dermis and can be safely used on the face or scalp. The skin is not visibly damaged and the micro-pores opened by the system close with one hour.

The technology also relates to variant forms of these sequences and/or of these fragments. The expression "variant" indicates a polypeptide or a peptide that differs, for example, from the sequence of a reference peptide while keeping its essential properties. Generally, the differences are limited so that the sequences of the reference peptide and those of the variant are quite similar and, in some regions, identical.

Preferentially, the variant forms are those which vary from reference sequences by the substitution of chemically equivalent (or homologous) amino acids, that is, by the substitution of a residue with another possessing the same characteristics. Thus, classical substitutions take place between Ala, Val, Leu and Ile; between Ser and Thr; between the acid residues Asp and Gln; and between the basic residues Lys and Arg, or between the aromatic residues Phe and Tyr.

The expression "variant" indicates a polypeptide or a peptide that differs, for example, from the sequence of a reference peptide while keeping its essential properties. Generally, the differences are limited so that the sequences of the reference peptide and those of the variant are quite similar and, in some regions, identical. A variant peptide and a reference peptide may differ in their amino acid sequence by one or several substitutions, additions, or deletions in all the combinations.

In the technology, the term "amino acid" refers to any natural or unnatural organic acid having the formula (II): —NHR—CR—C(O)—O (II), where each —R is independently selected from a hydrogen or an alkyl group having between 1 and 12 carbon atoms. Preferentially, at least an —R group of each amino acid is a hydrogen. The term "alkyl" refers to a carbon chain that can be linear or branched, substituted (mono- or poly-) or not substituted; saturated, mono-saturated (a double or triple bond in the chain), or poly-unsaturated (two or several double bonds, two or several triple bonds, one or several double bonds, and one or several triple bonds in the chain).

Many biologically compatible forms of protection can be considered, such as acylation or acetylation of the amino terminal end, or amidation or esterification of the terminal carboxyl end. Such forms are well known by those skilled in the art. Thus, the technology relates to the use as previously defined and is characterized by the fact that the peptide either is or is not in a protected form. Preferably, the protection used is either acylation or acetylation of the amino terminal group, or esterification or amidation of the terminal carboxyl end, or both of them. The amino acid derivatives and the peptide derivatives also relate to amino acids and peptides bound together by a pseudo-peptide bond. By the term "pseudo-peptide bond," we refer to all types of bonds likely to replace "classical" peptide bonds.

In the domain of amino acids, the geometry of the molecules is such that they can be theoretically presented as different optical isomers. There is indeed a molecular conformation of the amino acid (AA) such that it deviates to the right of the plane of polarization of the light (dextrorotatory conformation or D-aa), and a molecular conformation of the amino acid (aa) such that it deviates to the left of the plane of polarization of the light (levorotatory conformation or L-aa). Nature retained for the natural amino acids only levorotatory conformation. Consequently, a peptide of natural origin will be made up only of amino acids of type L-aa. However, chemical synthesis in a laboratory makes it possible to prepare amino acids having two possible conformations. From this basic material, it is thus possible to incorporate, during peptide synthesis, amino acids in the form of dextrorotatory or levorotatory optical isomers. Thus, the amino acids constituting the peptide according to the technology, can be under configuration L- and D-; in a preferential way, amino acids are in L configuration. The peptide according to the technology can be in L, D, or DL-configuration.

According to the technology, the peptides can be prepared using all appropriate methods. Thus, the peptides can be isolated peptides from peptides and proteins existing naturally, recombinant peptides, synthetic peptides, or peptides produced by a combination of these methods. Of course, the methods, in order to prepare the peptides according to the technology, are well known by one skilled in the art. Thus, the peptide according to the technology may be of natural or synthetic origin. Preferentially, according to the technology, the peptide is obtained by chemical synthesis.

According to an advantageous mode of embodiment of the technology, the abovementioned peptides are solubilized beforehand in one or several cosmetically or acceptable solvents classically used by one skilled in the art, such as water, ethanol, propylene glycol, butylene glycol, dipropylene glycol, ethoxylated or propoxylated diglycols, cyclic polyols, vaseline, a vegetal oil, or any combinations of these solvents. According to another advantageous mode of embodiment of the technology, the abovementioned peptides are solubilized beforehand in one cosmetic or vector such as liposomes, emulsions, solid lipid nanoparticles, micelles, micro- or nano-particles or adsorbed on powdery organic polymers, mineral supports like talcs and bentonites, and more generally solubilized in, or fixed on, any cosmetically or acceptable vector. The vector may be a particle with a range of sizes between 10 nm and 100 microns, more specifically 20 microns and 20 nm, and more specifically 15 microns and 100 nm. Particles may be composed of one or several excipients, including excipients generally regarded as safe (GRAS) by the FDA; phospholipids; saturated and unsaturated fatty acids and esters; PEGs of sizes from 100 g/mol to 20,000 g/mol, more specifically PEGs of 200 to 1200 g/mol, and more specifically PEGS of 400 to 600 g/mol; natural and unnatural polyamino acids having hydrophilic, hydrophobic, or chemically modified residues or some combination of these; synthetic and semisynthetic polymers such as HPMA, poly-lactic acid, and poly-esters; cyclodextrins; alcohols having one to 20 carbons; quaternary amines; lipids; fats; hydrophilic polymers; hydrophobic polymers; hydrogels; proteins; and any combination of the above or derivatives of the above. Further, particles may be engineered for uptake, delivery, or entrapment into the follicles, and the particles may limit or control the delivery of peptides or drugs into dermis surrounding the follicles, and the particles may limit or control the absorption of drugs or peptides into the blood, lymph, and systemic circulation and non-skin tissues.

It is of course obvious that the peptide according to the technology can be used alone or in association with at least one other active agent, in or for the preparation of a cosmetic and/or dermatological and/or pharmaceutical composition.

α-Tocopherol, a Vitamin E derivative, is a widely used additive in topical medications and cosmetics for its natural aesthetics. However, isolated cases have shown tocopherol may induce allergic contact dermatitis when frequently applied topically. Topical immunotherapy is a common method of treatment for acute cases of alopecia areata. The topical sensitizer is applied in increasing amounts to the inflicted skin, commonly the scalp, until an eczematous response is observed indicating sensitization to the material. Multiple theories on the mechanism of action of topical immunotherapy exist including the competitive antigenic inhibition of the auto immune response associated with alopecia areata upon allergic suppresser T cell generation. For this reason, addition of α-tocopherol to a formulation directed at treating alopecia related ailments could be beneficial. In one aspect, a micro or nano emulsion can include the tocopherol to enhance delivery of the peptide. Also, compositions having the peptide loaded into a particle can be formulated with the tocopherol.

In one embodiment, a particle having the peptide can be a certain size or within a certain size distribution. FIG. 14 show particle size data. The size and zeta potential can be important as they are factors that impact the absorption of the formulation and peptide topically. The formulation actually passes through the follicle and could be more properly called transappendageal drug delivery. Thus, one embodiment is transappendageal delivery and not transdermal delivery.

In one embodiment, the combination of a nano emulsion with the SPR4 peptide can allow for target delivery into the perifolicular region at the right concentrations where the peptide can have a therapeutic effect. Such delivery can avoid negative effects in a healthy individual that may occur if the peptide is given systemically (e.g., inhibits problems related to bone growth). Accordingly, localization and the correct peptide levels in those tissues may be important for a successful therapy. The emulsion may or may not have the peptide encapsulated in a particle.

If SPR4 is administered continuously (e.g., infusion) then there may be negative effects on bone. As such, one aspect of the invention is devoid of continuous infusion of the peptide. If administered intermittently (e.g., bolus) then the peptide has an anabolic or positive effect on-mineral metabolism and also glucose tolerance and insulin sensitivity. As such, one aspect of the invention allows for bolus administration. The SPR4-peptide does not cause osteosarcoma in mice.

Examples

SPR4-peptide was synthesized by Polypeptide Laboratories (San Diego Calif., USA 92126) with purity over 90%. Two batches of peptide were synthesized as follows: (1) Biotinylated (50 mg); and (2) non biotinylated (950 mg). The biotinylated form was to be used to assess dermal penetration of peptide following topical application using confocal microscopy. A novel model using a murine strain (B6CBAF1/J hybrid mouse) was developed and implemented.

L-α-Phosphatidylcholine (2.39 g/mL) was dissolved in ethanol. The solution was vortexed for 5 minutes and sonicated for 10 minutes or until a clear solution was achieved. Subsequently, SPR4 (5 mg/mL) was dissolved in PBS, pH 7.4, vortexed for 2 minutes and sonicated for 10 minutes or until dissolved. The SPR4 solution was added dropwise (1.5 mL/h) to the lipid ethanolic solution using syringe pump while constantly stirring. Then additional PBS (3.8× to SPR4 solution volume) was added dropwise (1.5 mL/h) using syringe pump while constantly stirring. The final solution was stored at 4° C. and covered from light exposure. The final formulation contained 103.8 mg/mL of lipid, 4.3% (v/v) of ethanol, and 0.99 mg/mL of SPR4.

L-α-Phosphatidylcholine/Cholesterol/1,2-dioleoyl-3-trimethylammonium-propane (DOTAP)/α-Tocopherol were dissolved in chloroform:methanol (2:1 (v/v)) to 8.35 mg/ml with a molar ratio of 55.7:34.3:8.6:1.3, PC:CH:DOTAP: α-Tocopherol. The solution was vortexed for 5 minutes and sonicated for 10 minutes or until a clear solution was achieved. SPR4 (0.165 mg/mL) was dissolved in 25 mM acetic acid with subsequent PBS, pH 7.4 addition (1:9, AcOH:PBS). The SPR4 solution was added dropwise (1.5 mL/h) to the lipid solution using syringe pump while constantly stirring until a 6:1 solvent-to-buffer ratio was achieved. The solution was then sonicated for 2-5 minutes or until clear. If mixture was not clear after sonication, methanol was added to no more than 10% of the total volume. Subsequently, organic solvents were removed by rotoevaporation. Solvent removal continued until all foaming within the mixture ceased. The final solution was stored at 4° C. and covered from light exposure. The final formulation contained 50 mg/mL of lipid and 0.99 mg/mL of SPR4.

L-α-Phosphatidylcholine/Cholesterol/1,2-dioleoyl-3-trimethylammonium-propane (DOTAP)/α-Tocopherol were dissolved in ethanol to 125 mg/ml with a molar ratio of 55.7:34.3:8.6:1.3, PC:CH:DOTAP: α-Tocopherol. The solution was vortexed for 5 minutes and sonicated for 10 minutes or until a clear solution was achieved. SPR4 (1.73 mg/mL) was dissolved in 25 mM acetic acid with subsequent PBS, pH 7.4 addition (1:9, AcOH:PBS). The lipid ethanolic mixture was heated to 65° C. for 2-3 min and the SPR4 solution heated to 37° C. for 2-3 min. The lipid mixture was added dropwise to the SPR4 solution while constantly stirring until a 2:3 solvent-to-buffer ratio was achieved. Subsequently, the solution was passed ten times through a 100 nm polycarbonate filter and dialyzed against PBS for 24 hours to remove excess ethanol. Ethanol was added to 4.3% (v/v) following dialysis. The final solution was stored at 4° C. and covered from light exposure. The final formulation contained 50 mg/mL of lipid, 4.3% (v/v) of ethanol and 0.99 mg/mL of SPR4.

Glyceryl dilaurate/Cholesterol/Polyoxyethylene (10) stearyl ether (POE-10)/1,2-dioleoyl-3-trimethylammonium-propane (DOTAP)/α-Tocopherol were mixed with a weight ratio of 50:14:23:12:1, GDL:CH:POE-10:DOTAP:α-Tocopherol and melted at 70° C. The lipid melt was then filtered through a 0.22 μm filter and reheated to 70° C. prior to being drawn into a sterile syringe. A second syringe containing PBS was heated to 65° C. and attached to a three way stopcock with the lipid mixture syringe. The aqueous phase was slowly injected into the lipid phase syringe. Subsequently, the mixture was rapidly passed back and forth between the two syringes while being cooled under water until reaching room temperature. The mixture was then sonicated for 20 min. SPR4 (2.0 mg/mL) was dissolved in 25 mM acetic acid with subsequent PBS, pH 7.4 addition (1:9, AcOH:PBS). Equal volumes of the empty liposome solution and SPR4 solution were mixed and incubated at room temperature for 45 min. The final solution was stored at 4° C. and covered from light exposure. The final formulation contained 50 mg/mL of lipid and 1 mg/mL of SPR4.

Glyceryl dilaurate/Cholesterol/Polyoxyethylene (10) stearyl ether (POE-10)/1,2-dioleoyl-3-trimethylammonium-propane (DOTAP)/α-Tocopherol were mixed with a weight ratio of 50:14:23:12:1, GDL:CH:POE-10:DOTAP:α-Tocopherol and melted at 70° C. The lipid melt was then filtered through a 0.22 μm filter and reheated to 70° C. prior to being drawn into a sterile syringe. A second syringe containing PBS was heated to 65° C. and attached to a three way stopcock with the lipid mixture syringe. The aqueous phase was slowly injected into the lipid phase syringe. Subsequently, the mixture was rapidly passed back and forth between the two syringes while being cooled under water until reaching room temperature. The mixture was then sonicated for 20 min. SPR4 (2.0 mg/mL) was dissolved in 25 mM acetic acid with subsequent PBS, pH 7.4 addition (1:9, AcOH:PBS). Equal volumes of the empty liposome solution and SPR4 solution were mixed and incubated at room temperature for 45 min. Ethanol was added to 4.3% (v/v). The final solution was stored at 4° C. and covered from light exposure. The final formulation contained 50 mg/mL of lipid, 4.3% (v/v) of ethanol and 1 mg/mL of SPR4. Glyceryl dilaurate/Cholesterol/Polyoxyethylene (10) stearyl ether (POE-10)/1,2-dioleoyl-3-trimethylammonium-propane (DOTAP)/α-Tocopherol were mixed with a weight ratio of 50:14:23:12:1, GDL:CH:POE-10:DOTAP:α-Tocopherol and dissolved in ethanol to (33 mg/ml). The solution was vortexed for 5 minutes and sonicated for 10 minutes or until a clear solution was achieved. Subsequently, SPR4 (1 mg/mL) was dissolved in PBS, pH 7.4, vortexed for 2 minutes and sonicated for 10 minutes or until dissolved. The SPR4 solution was added dropwise (1.5 mL/h) to the lipid ethanolic solution using syringe pump while constantly stirring. Subsequently, ethanol was removed by rotoevaporation. The final solution was stored at 4° C. and covered from light exposure. The final formulation contained 50 mg/mL of lipid, 0% (v/v) of ethanol, and 0.99 mg/mL of SPR4.

Glyceryl dilaurate/Cholesterol/Polyoxyethylene (10) stearyl ether (POE-10)/1,2-dioleoyl-3-trimethylammonium-propane (DOTAP)/α-Tocopherol were mixed with a weight ratio of 50:14:23:12:1, GDL:CH:POE-10:DOTAP:α-Tocopherol and dissolved in ethanol to (33 mg/ml). The solution was vortexed for 5 minutes and sonicated for 10 minutes or until a clear solution was achieved. Subsequently, SPR4 (1 mg/mL) was dissolved in PBS, pH 7.4, vortexed for 2 minutes and sonicated for 10 minutes or until dissolved. The SPR4 solution was added dropwise (1.5 mL/h) to the lipid ethanolic solution using syringe pump while constantly stirring. Subsequently, ethanol was removed by rotoevaporation. Ethanol was added to 4.3% (v/v). The final solution was stored at 4° C. and covered from light exposure. The final formulation contained 50 mg/mL of lipid, 0% (v/v) of ethanol, and 0.99 mg/mL of SPR4.

The encapsulation efficiency of the SPR4 into a liposome was determined as stated below. A known volume of the final liposome solution was centrifuged at 15,000×g for 15 min. The supernatant, unencapsulated SPR4, was removed and placed in a new centrifuge cuvette and the pellet, encapsulated SPR4, was retained. This procedure was repeated twice or until a pellet was no longer visible after centrifugation. The supernatant was sufficiently diluted with PBS and the concentration of SPR4 determined by RP-HPLC against a known standard concentration profile. The pellets were combined and dissolved in ethanol and the concentration of SPR4 determined by RP-HPLC against a known standard concentration profile. This procedure was repeated for all formulations.

Example for Production of Empty Liposomes.

The liposome vesicle was formulated with the core starting material L-α-phosphatidylcholine from egg yolk, ethanol as a penetration enhancer and phosphate buffered saline (PBS) to stabilize the vesicle in solution: Measure 377.4 mg Egg-PC (L-α-phosphatidylcholine); Add 157.8 uL Ethanol (200 Proof); Vortex mixture (~5 min) and sonicate mixture (~10 min) until Egg-PC fully dissolved; Add 3360.0 uL PBS, pH 7.4, dropwise while constantly stirring. PBS dispersed via an auto syringe instrument at 1.5 mL/h.; and Store at 4° C., covered from light exposure.

Example of Peptide Loaded Liposomes

The SPR4 peptide was formulated in the vesicles: Measure 377.4 mg Egg-PC (L-α-phosphatidylcholine); Add 157.8 uL Ethanol (200 Proof); Vortex mixture (~5 min) and sonicate mixture (~10 min) until Egg-PC fully dissolved; Add 720 uL peptide solution (5 mg/mL) dropwise while stirring; Peptide stock (5 mg/mL) solution; Measure 4.06 mg dried peptide; Add 812 uL PBS (ph 7.4); Vortex for 2 min; Sonicate for ~10 min or until peptide fully dissolved; Store at −20° C., covered from light exposure; Add 2760 uL PBS, pH 7.4, dropwise while constantly stirring. PBS dispersed via auto syringe instrument at 1.5 mL/h; and Store at 4° C., covered from light exposure.

Lysine modified chitosan example: Reference: Biomaterials 31 (2010) 4129-4138. First, lysine modified chitosan (LMC) is prepared as follows. 0.11 g of chitosan was dissolved in 10 mL dd H2O, followed by addition of 5 mL HCl (3 mol/L). Butyloxycarbonyl modified lysine, EDC, and DMF are consequently added into the solution under stirring. Polymerization was carried out at 25 C overnight. Then the butyloxycarbonyl groups are removed by the addition of TEA. The product is centrifuged and washed with ethanol three times. Subsequently, peptide is reacted with the lysine modified chitosan in the presence of EDC at pH 5. The reaction is carried out with stirring for 24 hours. The resulting peptide polymer conjugates were dialyzed again water for 48 hours with 4 water changes.

Calcium phosphate method: Reference: International Journal of Pharmaceutics 250 (2003) 25. First, sodium bis(ethylhexyl)sulphosuccinate (SBS, 0.1 M) in hexane solution was prepared. Ten milliliters of CaCl2 (20% w/v), 80 mL dd H2O and 1 mL of peptide solution were dissolved by continuous stirring for 48 h to form solution A. Second, another SBS in hexane solution was prepared. Ten milliliters of Na2HPO4 (5% w/v), 70 mL of dd H2O and 1 mL of peptide were dissolved by continuous stirring for 48 h to form solution B. Third, solution B was slowly added to solution A with continuous stirring for 6 h. The resulting nanoparticles are centrifuged for 30 min at 1000 rpm and washed with hexane three times. Finally it was redispersed in 5 ml of dd H2O by sonication.

Conjugate peptide to low-molecular-weight protamine: Reference: J Pharm Sci. 2013 November; 102(11):4109-20. Peptide is conjugated via a degradable linker, such as an ester or hydrazone, to protamine polymer. The protamine may be of a size of x to x. An amide linkage between the protected peptide can be made using EDAC/NHS chemistry to conjugate the C-terminus an amine of protamine, followed by deprotection. A hydrazone can be formed by conjugate of an aldehyde group to the N or C terminus of the peptide followed by formation of the Schift base under mild acid conditions (e.g. pH 3-5), followed by purification by a means such as dialysis or solvent precipitation. The ester can be formed using the C terminus or a side chain (such as aspartic or glutamic acid) and an alcohol conjugated to the protamine.

FIG. 1 shows suppression of circulating sclerostin in wild type mice infused with SPR4 using osmotic pump infusion. Here, male (5-week) C57B/L6 mice were used for the study represented in FIGS. 1 to 3. All mice were maintained on a 1% phosphorus and 2.4 IU/g Vitamin-D3 diet (Harlan Teklad Rodent Diet 8604, Indianapolis, Ind.). Mice (5 week) were surgically implanted with Alzet osmotic pumps (Durect Corporation, Cupertino, Calif.) and infused with SPR4-peptide (276 nmoles/hr/kg) or vehicle (0.9% physiological Saline; VE) for 28 days. Specifically, SPR4 peptide was dissolved as follows: (1) 200 µg of peptide (SPR4) is first dissolved in 20 µL of 25 mM acetic acid, (2) 180 µL of 50 mM Tris pH7.4/150 mM NaCl is then added, (4) 4 µL of 1 mM $ZnCl_2$ is added last (note $ZnCl_2$ can be added after the peptide is dissolved in aqueous solutions 1 and 2 to prevent precipitation of peptide). The SPR4 peptide was first completely dissolved in 25 mM acetic acid (20 µg/uL) followed by the addition of 50 mM Tris pH7.4/150 mM NaCl to give a final concentration of 2 ug/uL. Finally, $ZnCl_2$ from a stock 1 mM solution was added to give a final concentration of 20 uM $ZnCl_2$. The procedure was found to dissolve peptide and the addition of $ZnCl_2$ was done last because earlier additions of $ZnCl_2$ result in precipitation of peptide. Alzet pump model #2004 with a constant infusion rate of 0.25 uL/h over 28 days was used. 2 groups were studied (n=6/group); (1) Wild type mice infused with vehicle (WT-VE), and (2) Wild type mice infused with SPR4 peptide (WT-SPR4)

At specific intervals throughout the experiment as detailed in the results section tail blood-samples were collected in serum-separator tubes. On the final day of the infusion experiment (day 28) blood and urine were collected from mice fasted overnight in metabolic cages with full access to water (1 cage/mouse). The blood from the final bleed was collected by cardiac exsanguination and serum urinalysis. Briefly, Osteocalcin (Mouse Osteocalcin EIA Kit; BTI, Stoughton, Mass.), alkaline phosphatase (Liquid Alkaline Phosphatase; Pointe Scientific Inc, Canton, Mich.), 1.25 (OH)2D3 (IDS Inc., Fountain Hills, Ariz.) and FGF23 (Kainos Laboratories Inc., Tokyo, Japan) were measured on serum samples. Inorganic phosphorus, calcium, creatinine (Pointe Scientific Inc, Canton, Mich.) and Osteopontin (Quantikine Mouse Osteopontin; R&D Systems, Minneapolis, Minn.) levels were assessed both in serum and urine. A competitive ELISA kit was used for the peptide measurement. Circulating sclerostin (SOST) was measured using a commercially available ELISA kit purchased from ALPCO Diagnostics (Keewaydin Drive, Salem, N.H. 03079, USA).

FIG. 2 shows suppression of sclerostin in wild type mice cortical bone (femurs) as measured using immunohistochemistry (IHC) following infusion of SPR4. SPR4 and vehicle were infused using osmotic pumps as discussed. It was found that (A Images) sclerostin protein-expression (brown-stain) in femur bone-sections is localized to osteocytes (see arrows) and markedly suppressed in SPR4 treated mice (e.g., compare photos in Panels 1 and 2 of A Images). Magnifications are 60× and are from representative cortical femur sections (matched regions). It was found that (B Images) sclerostin protein-expression (brown-stain) in renal cortex sections is markedly suppressed in SPR4 treated mice (e.g., compare photos 1 and 2 of B Images). Staining is localized to renal tubules with little glomerular staining. Magnifications are 20× and are from representative sections (matched regions). Immunohistochemistry was carried out. Specifically, proximal tibias and distal femurs were decalcified in 0.1 M EDTA aqueous solution for 2 weeks until complete demineralization. Decalcified bones and left kidneys were dehydrated in absolute ethanol and embedded in paraffin. 5 µm thick sections were cut on a rotary microtome. Sections were dried overnight on pre-charged pre-cleaned slides (VWR Scientific, PA, USA), de-paraffinized and rehydrated. For immunohistochemistry, after antigen retrieval by incubation in citric acid buffer 10 mM pH 3 for 60 minutes at 37° C., nonspecific sites were blocked with 1× animal free blocker (Vector Laboratories Inc., CA, USA) and then sections were incubated with specific primary antibodies for 1 hour. An Immunohistological Vectastain ABC kit (Vector Laboratories Inc., CA, USA) is routinely used and slides counterstained with DAPI or methyl-green, dehydrated and mounted with entellan. Polyclonal primary antibodies and the in situ hybridization was performed. Probes were labeled with fluorescein tag using the FastTag Basic Labeling Kit and detected with an alkaline phosphatase anti-fluorescein (Vector Laboratories Inc., CA, USA) antibody according to the manufacturer's instructions.

FIG. 3 show increased active β-catenin protein-expression in wild type mice cortical bone (femurs) as measured by western-blotting following infusion of SPR4. SPR4 and vehicle were infused using osmotic pumps as described in connection with FIG. 1. The increased active β-catenin as illustrated by calculating the ratio of active (e.g., nonphosphorylated) and inactive phosphorylated β-catenin is consistent with the suppressed sclerostin shown in FIGS. 1 to 4. Western analysis of protein lysates prepared from femurs frozen in LN2 were undertaken. Each lane was loaded with same amount of protein for each sample. Transferrin was used as an internal control for chemiluminescent pixel density calculations (BioRad Qtyl software and FluorS MaX Imaging). One way Anova and Newman-Keuls Post Test was used to calculate statistical significance ($P<0.01^*$ and $P<0.001^{**}$).

Some data shows the decreased expression of sclerostin (SOST) mRNA from bone (femurs) with changes in expression of other genes in mice infused with SPR4. Additional data shows the decreased expression of sclerostin (SOST) mRNA from whole kidneys with changes in expression of other genes in mice infused with SPR4.

Figure 4:
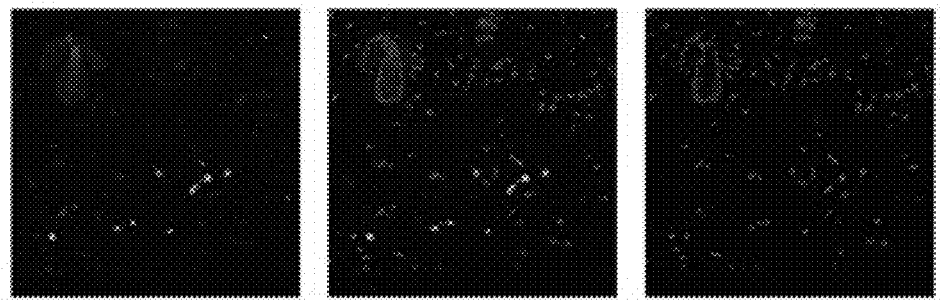
FIG. 4 shows murine dermal penetration of fluorescently labeled SPR4 as measured using laser confocal microscopy.
Figure 4:
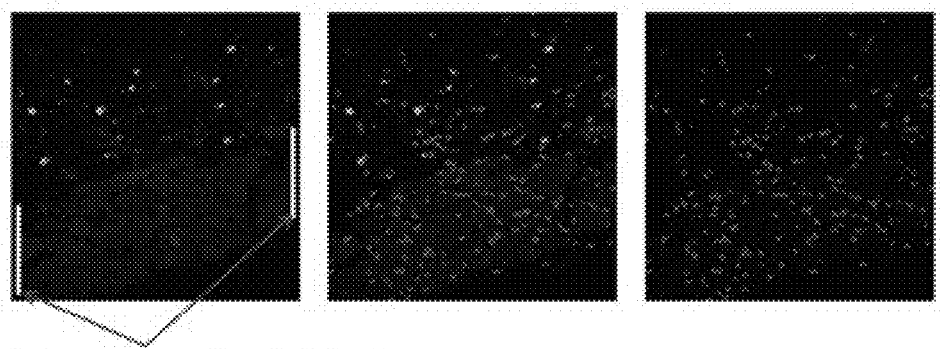
Figure 4:
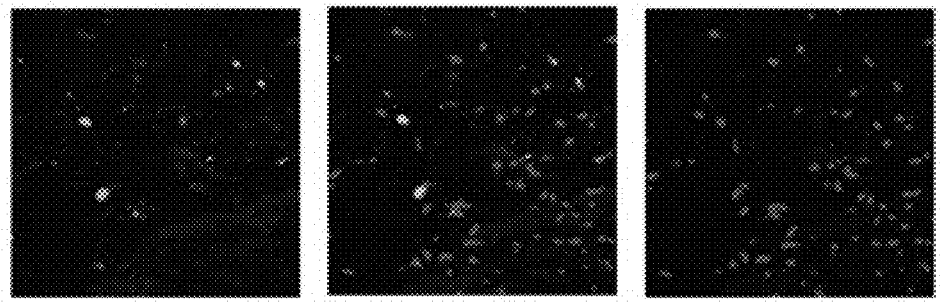

FIG. 4 shows murine dermal penetration of fluorescently labeled SPR4 as measured using laser confocal microscopy. SPR4 is visualized by the green color and nuclear DAPI-staining blue. Rows A, B, C depict different magnifications and dermal layers as indicated in the figure. The left and right pictures of Rows A, B and C are SPR4 and DAPI nuclear stained images respectively and the middle pictures are merged images. SPR4 peptide (1 mg) was fluorescently labelled using a commercially available kit purchased from Thermo Scientific (#53024, DyLight™ 488 Antibody labeling kit ($A_{max}$ 493 nM); Pierce Biotechnology, Rockford, Ill. 61105 USA). A liposome peptide formulation was prepared as described in connection to FIGS. 6 and 50 μL applied to anagen phase induced dorsal-hair depilated mice (also FIG. 6). Mice were euthanized after 30 min and paraffin sections of 10% neutral buffered formalin (4% formaldehyde in phosphate buffered saline) fixed skin prepared for histology.

Figure 5:
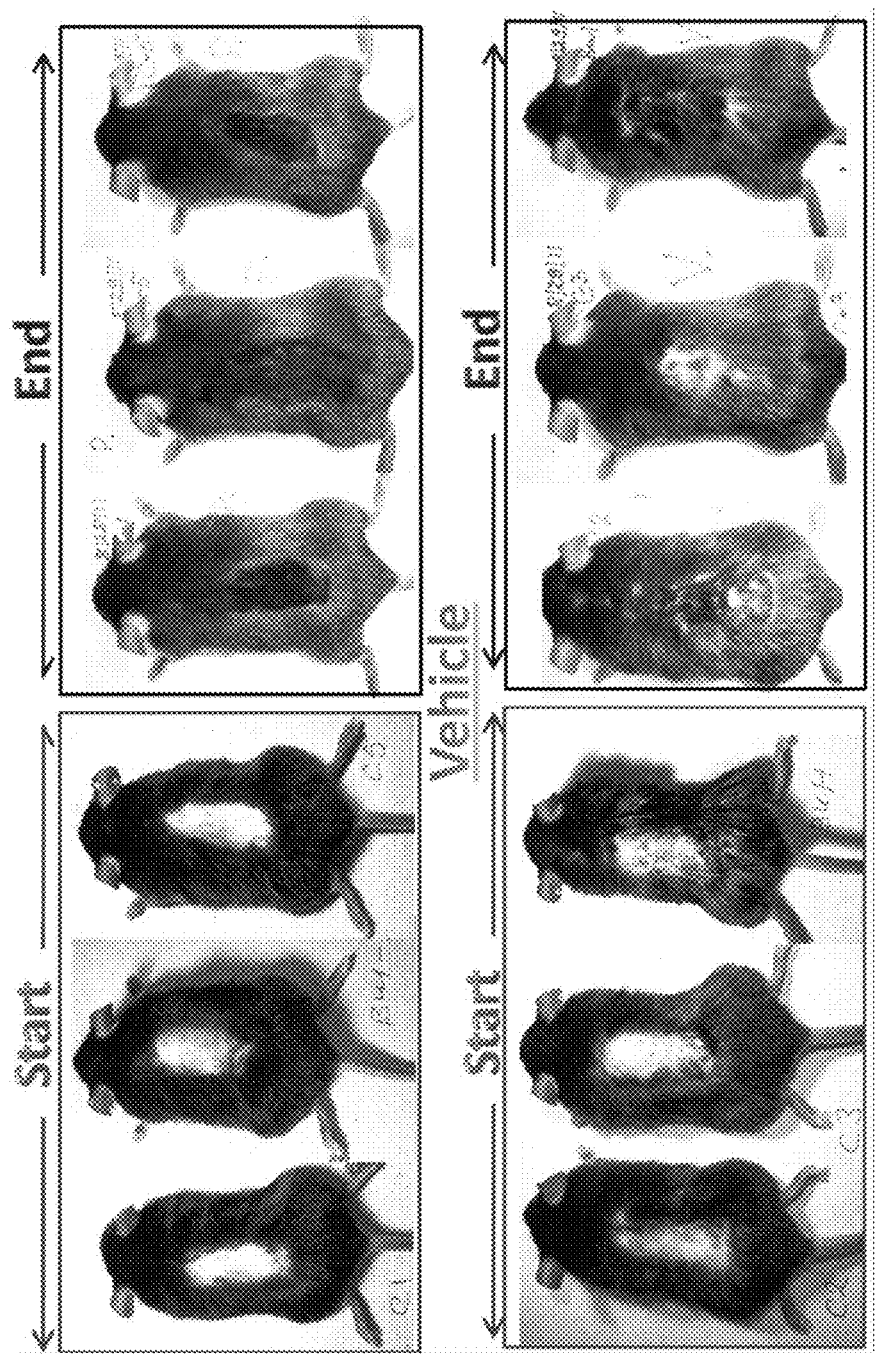
FIG. 5 shows accelerated hair growth in depilated mice (N=6) treated with repeat localized intradermal (i.d) injections of SPR4 over 11 days.

FIG. 5 shows accelerated hair growth in depilated mice (N=6) treated with repeat localized intradermal (i.d) injections of SPR4 over 11 days. Specifically, SPR4 peptide was dissolved as follows; 200 μg of peptide (SPR4) is first dissolved in 20 μL of 25 mM acetic acid, 180 μL of 50 mM Tris pH 7.4/150 mM NaCl is then added, 4 μL of 1 mM $ZnCl_2$ is added last (note $ZnCl_2$ should be added after the peptides is dissolved in aqueous solutions 1 and 2 to prevent precipitation of peptide). This gives a final concentration of 0.98 mg/mL (SPR4) in 44 mM Tris pH7.4/132 mM NaCl/19.6 μM $ZnCl_2$. Single 100 uL i.d injections (98 μg) were give each day of dissolved SPR4 peptide (experimental) or vehicle (44 mM Tris pH7.4/132 mM NaCl/19.6 μM $ZnCl_2$). Anagen phase in 5 week old mice wild type mice (C57BL/6) was induced by depilation of their dorsal hair using Wax Strips (Del Laboratories, Farmingdale, N.Y.) following the manufacturer's instructions.

Figure 6:
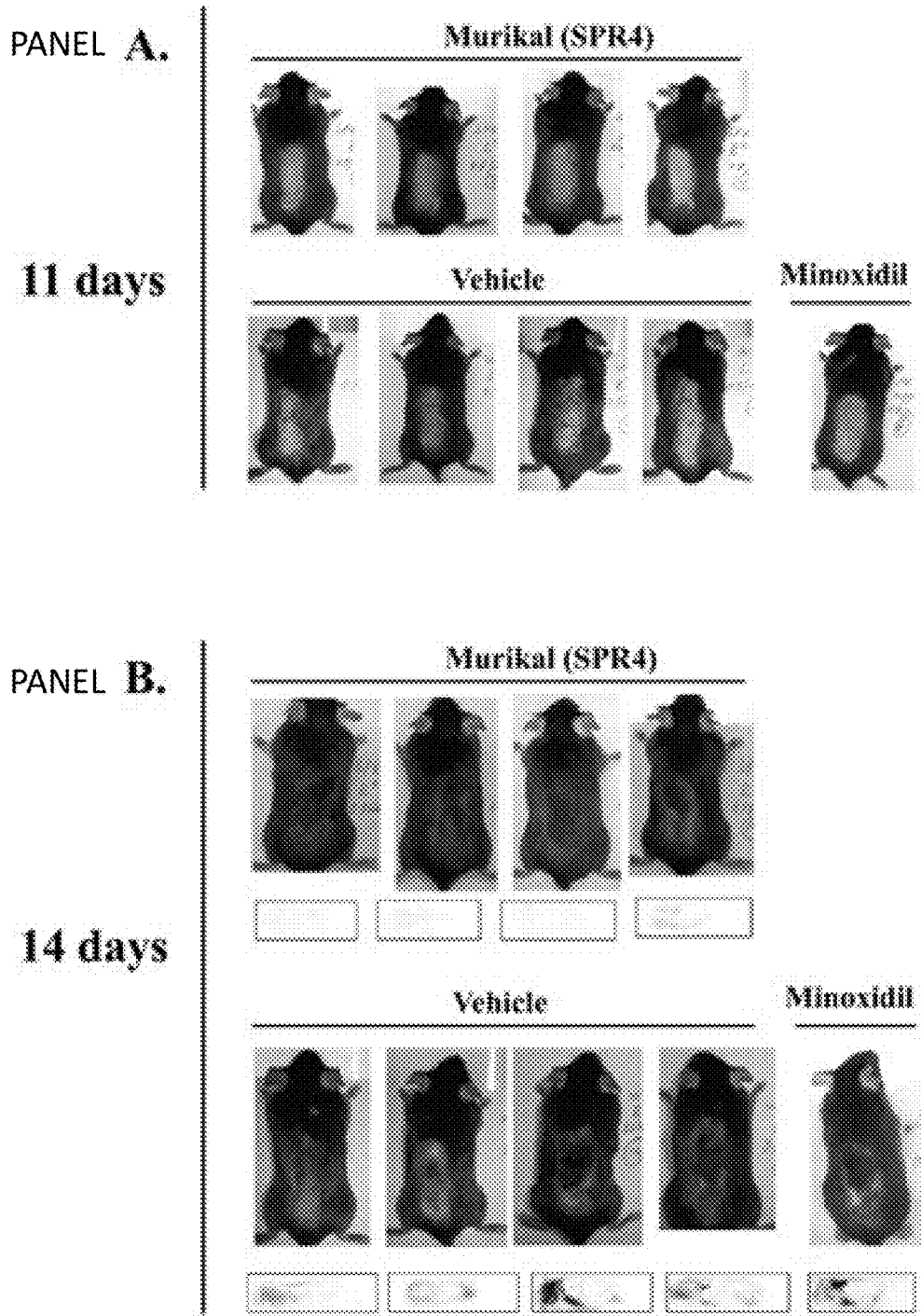
FIG. 6 shows accelerated hair growth in anagen induced depilated mice topically treated with daily liposome formulations of SPR4 (50 μL).

FIG. 6 shows accelerated hair growth in anagen induced depilated mice topically treated with daily liposome formulations of SPR4 (50 μL). As described in FIG. 5 anagen phase in 5 week old mice wild type mice (C57BL/6) was induced by depilation of their dorsal hair using Wax Strips (Del Laboratories, Farmingdale, N.Y.) following the manufacturer's instructions. Note, the hair growth in minoxidil (rogaine) treated mice was not appreciably different to vehicle treated mice. Controls were treated with empty liposome vehicle formulations and the procedures for SPR4 in loaded vehicle formulations.

Figure 7:
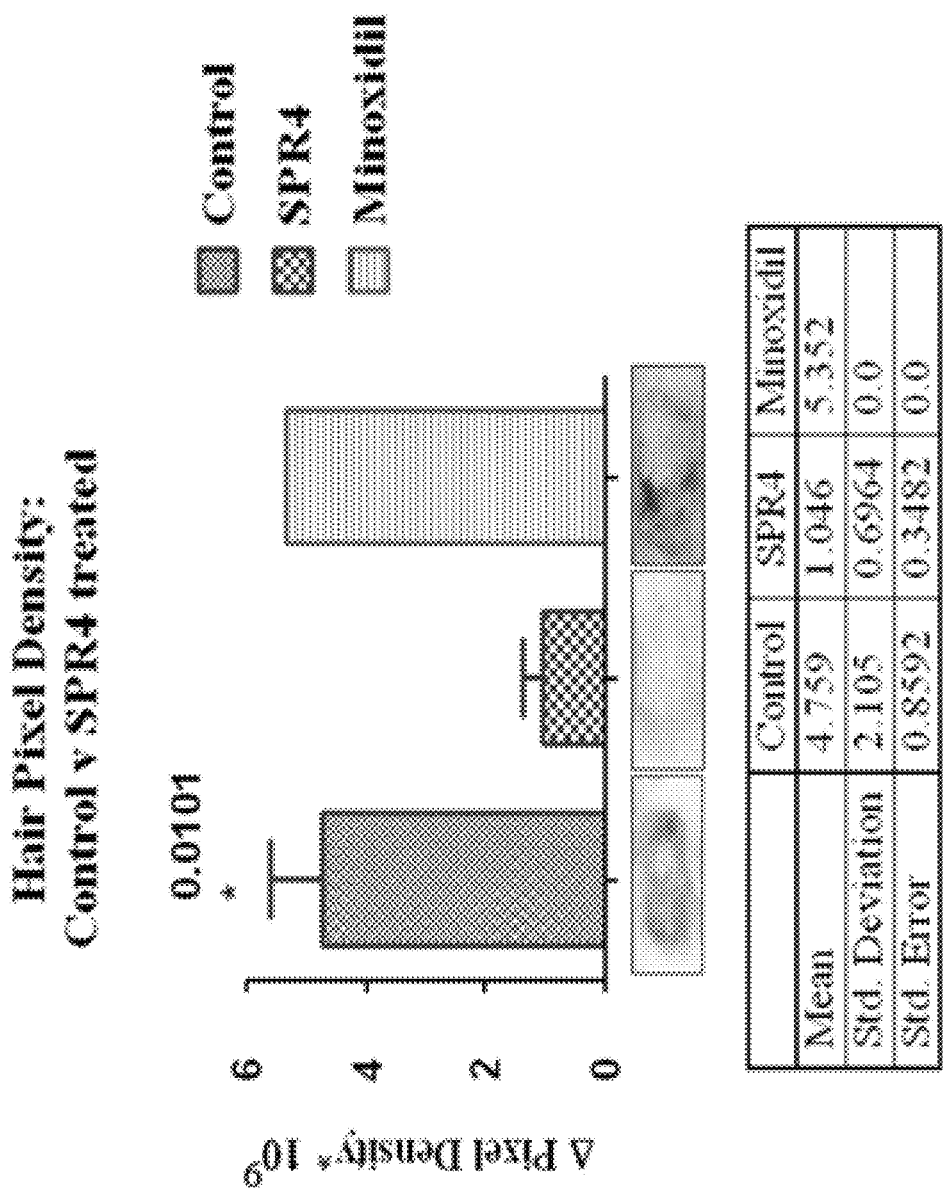
FIG. 7 shows data for contrast-images from FIG. 6 were digitally quantitated using a pixel conversion program Gel-Quant.Net (BiochemicalLabSolutions.com).

FIG. 7 shows data for contrast-images from FIG. 6 were digitally quantitated using a pixel conversion program Gel-Quant.Net (BiochemicalLabSolutions.com). The lower the reading the greater the hair density/growth occurring. Note, mice treated with SPR4 had a significant and major increase in hair density/growth compared to both vehicle and minoxidil treated mice. Also, there was no significant difference between minoxidil and control treated mice.

It was found that an overexpression of the enzyme 5-α reductase and thus increased conversion of testosterone to 5-α-dihydrotestosterone (5α-DHT) plays a major role in the development of androgenetic alopecia (ADA). To exploit this pathway we used B6CBAF1/J hybrid male mice reported to be susceptible to ADA. As a control and to remove background testosterone effects all the B6CBAF1/J hybrid male mice were castrated and split into two groups (n=6). The first group served as controls (Vehicle) and the second experimental group was treated with 5-α-dihydrotestosterone (5α-DHT). The 5α-DHT was administered by sub-dermal transplantation of slow release pellets purchased from Innovative Research of America. The control group was also transplanted with identically formulated placebo pellets (without 5α-DHT). Both pellets were transplanted below the right ear using a small incision that was sealed with staples. Specifically, two 21 day release and one 90 day release pellets containing 10 mg of 5α-DHT respectively were used for each experimental mouse with corresponding placebo pellets for the controls (n=6). Hair loss of the mice and the effects of 5α-DHT were then monitored over 5 months as described below.

It was found that 5α-DHT mice have increased bone mineral density (BMD) and weight & lean mass. Using dual energy x-ray absorptiometry (DEXA) we showed that castrated mice treated with 5α-DHT had major increases in weight and Bone Mass (Bone mineral Density [BMD] and Bone Mineral Content [BMC]).

FIGS. 8A-8B includes DEXA analysis pictures of representative Vehicle and 5α-DHT male castrated mice showing increased bone and lean mass with treated mice. The graph shows an increase in weight in mice treated with 5α-DHT over the 5 months of the study. Two-way ANOVA analysis of the temporal weight change show significant differences for 5α-DHT treatment (p<0.0001) and change over time (p<0.0001) with no significant interaction (n=6). This confirms 5α-DHT pellet infusion was effective (see also below). A pictorial representation of the DEXA analysis with changes in weight are shown in FIG. 8B.

Figure 9:
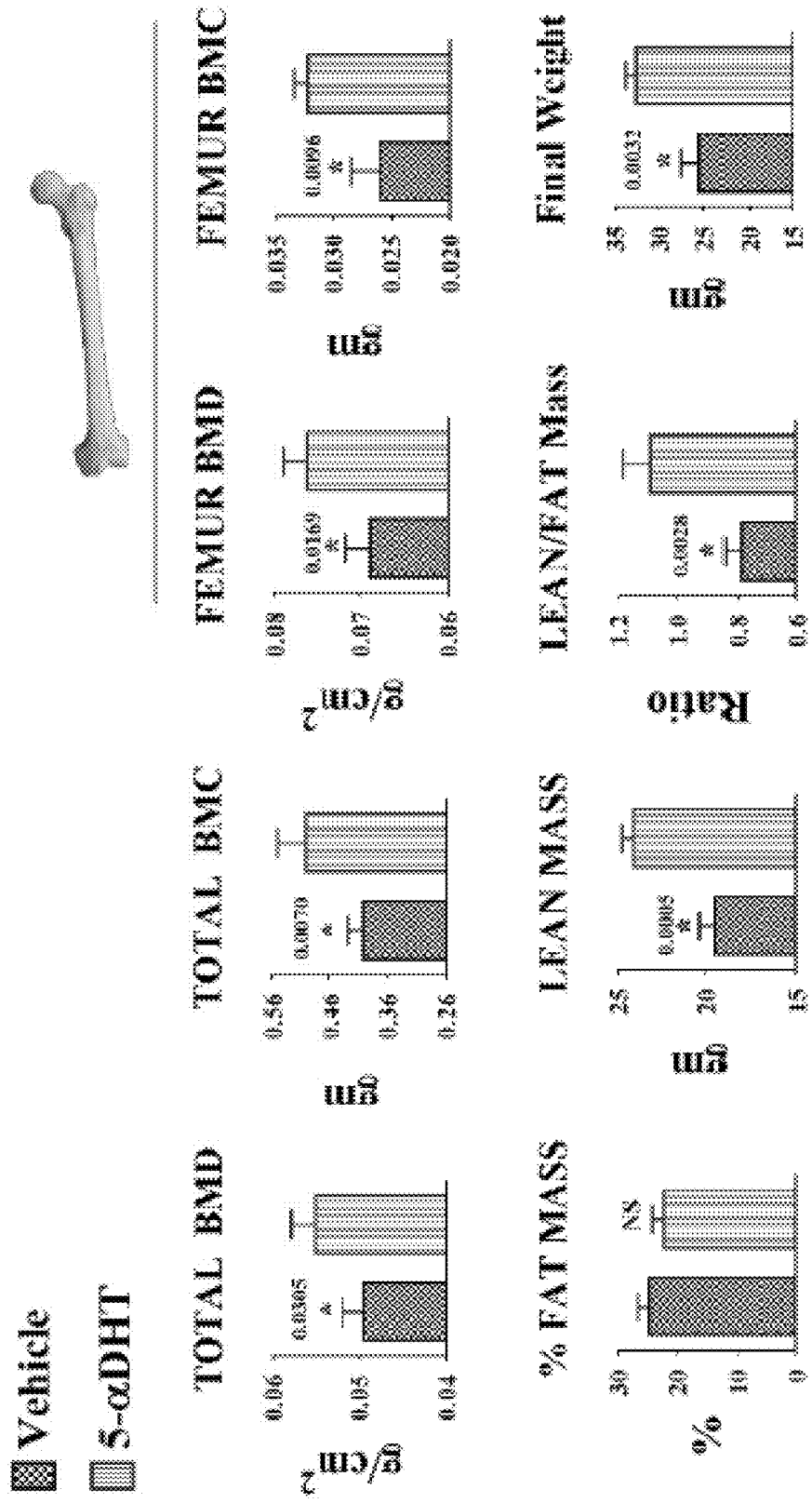
FIG. 9 shows castrated male mice infused with 5α-DHT show increased bone mass, mineral content, lean mass and lean/fat mass ratios compared to vehicle infused castrated male mice (n=6).

Detailed quantitative analyses of the DEXA experiments are presented graphically in FIG. 9. FIG. 9 shows castrated male mice infused with 5α-DHT show increased bone mass, mineral content, lean mass and lean/fat mass ratios compared to vehicle infused castrated male mice (n=6). Total and femur analyses are shown and the numbers shown on the histograms above the asterisks (*) are p values calculated using a two-tailed unpaired t test at 95% confidence intervals. A P<0.05 is considered significant and NS indicates not significant.

These data confirm statistically significant changes in bone mass, lean mass and lean/fat mass ratios and show 5α-DHT infusion of castrated male mice is effective. Further high resolution confirmation of 5α-DHT induced changes to bone were acquired by micro computed tomographic (XT) analyses of femurs. Three dimensional illustrations of these changes are shown in FIG. 3. The 3D images show major increases in cancellous bone and trabecular architecture at the top of the epiphyses. Thus infusion of 5α-DHT corrects the bone loss and abnormal bone occurring in castrated male mice (FIG. 10).

Figure 10:
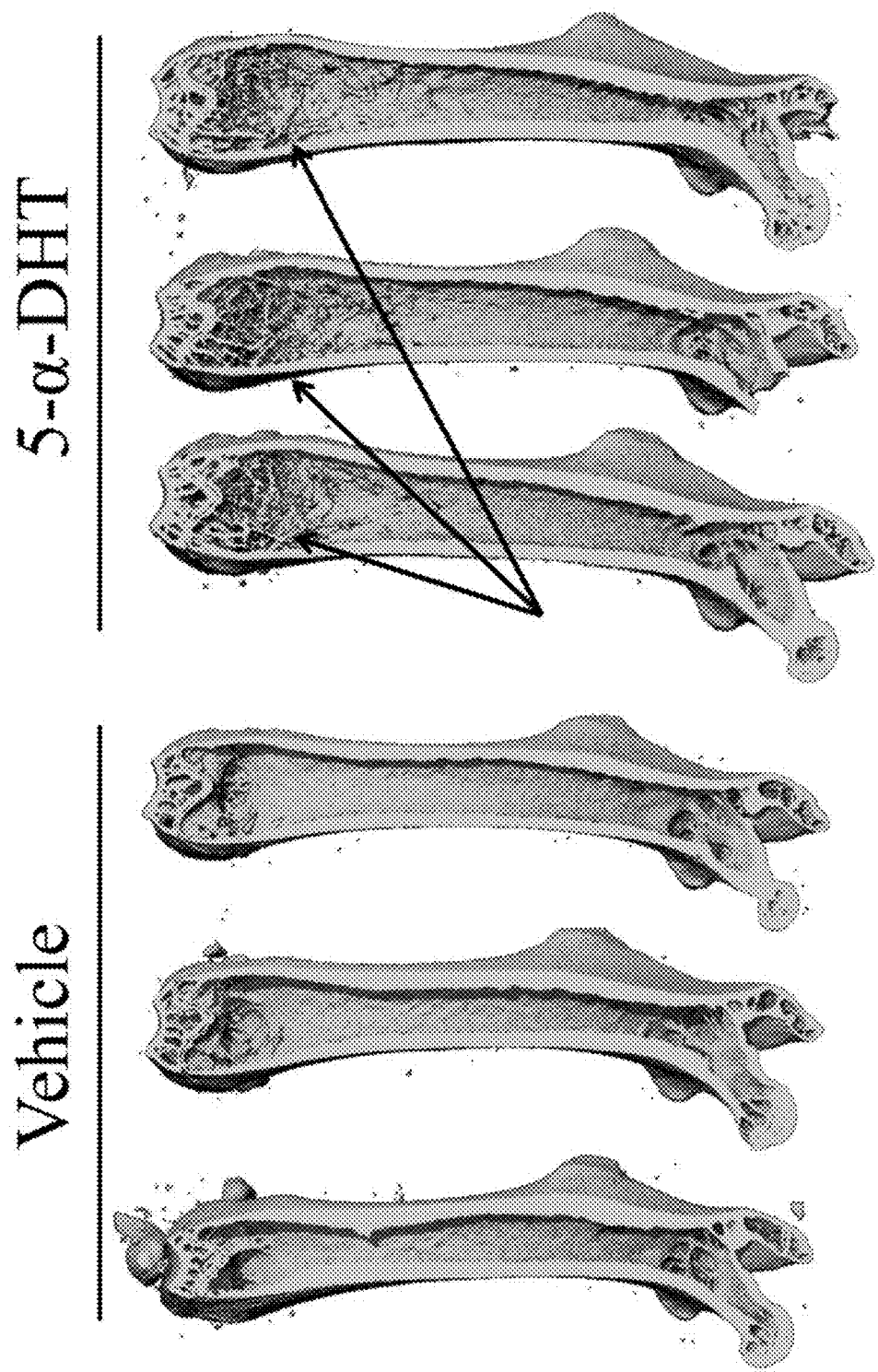
FIG. 10 shows high resolution (6 uM) 3D μCT images of femurs from vehicle and 5a-DHT treated castrated male mice. The arrows highlight the massive increase in cancellous and trabecular bone in the epiphyses of experimental mice.

FIG. 10 shows high resolution (6 uM) 3D μCT images of femurs from vehicle and 5α-DHT treated castrated male mice. The arrows highlight the massive increase in cancellous and trabecular bone in the epiphyses of experimental mice.

Figure 11:
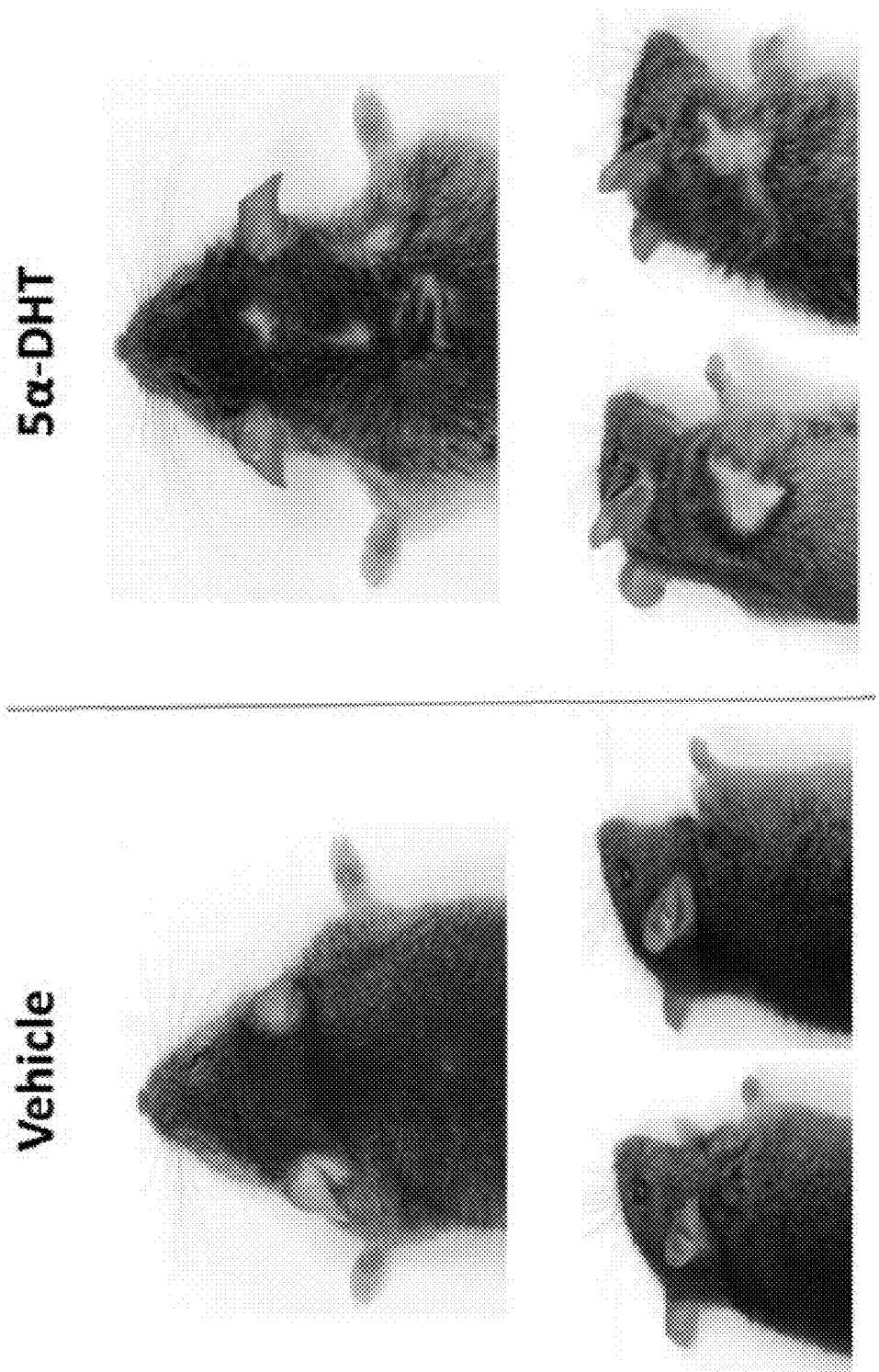
FIG. 11 includes representative pictures of male castrated mice treated with vehicle or 5α-DHT.

In summary these experiments demonstrate and confirm the effectiveness of 5α-DHT infusion by sub-dermal pellet in castrated male mice. Castrated male mice infused with 5α-DHT develop androgenetic alopecia (AGA) were used in the studies. To determine whether 5α-DHT infusion induced hair loss, mice were photographed with high resolution cameras over 5 months of treatment and compared with vehicle (placebo pellet) controls. Lighting, focal length, camera lens and camera were kept the same. Also, mice were placed on a template and kept in the same order to ensure reproducibility and photographic image consistency. Photographs were then analyzed using ADOBE Photoshop software and quantified and compared by measuring integrated pixel density. The regions compared and measured were of the same dimensions and encompassed identical locations on the head and dorsal region of the shoulder blades. Of note, hair from the region surrounding placebo pellet implantation grew well but this contrasted dramatically with the 5α-DHT implant region (see FIG. 11). FIG. 11 includes representative pictures of male castrated mice treated with vehicle or 5α-DHT. Note hair loss from head and shoulders with experimental mouse. Also, the implant site shows major hair loss in mice treated with 5α-DHT mice but was normal with placebo mice.

Figure 12:
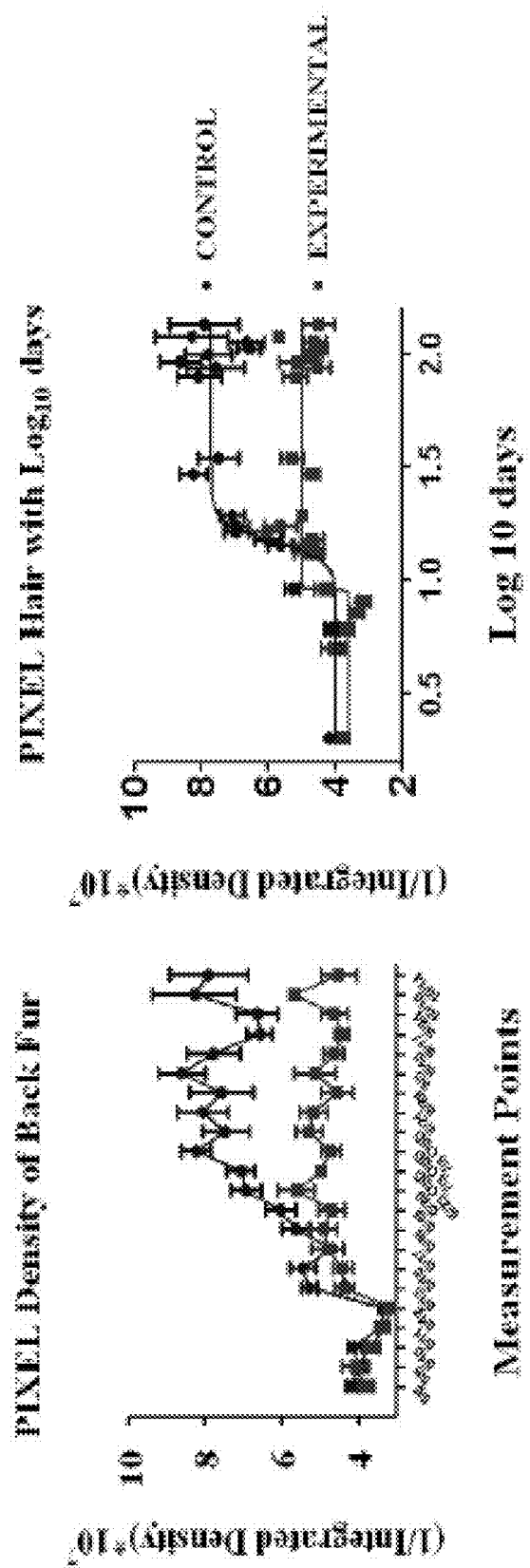
FIG. 12 shows accelerated hair loss occurred with male mice treated with 5a-DHT with an inflection point after 2 months.

The hair loss from the head and shoulder blade region is also shown in FIG. 4 and FIG. 12 graphically and quantitatively depicts the reduced hair loss in mice infused with 5α-DHT. FIG. 12 shows accelerated hair loss occurred with male mice treated with 5α-DHT with an inflection point after 2 months. Photographs were analyzed using ADOBE Photoshop. The inverse function of the integrated pixel density is shown on the X-axis (the lower the numbers the less hair). Two-way ANOVA analysis of the temporal inverse integrated pixel density showed significant differences for 5α-DHT treatment ($p<0.0001$) and change over time ($p<0.0001$) with significant interaction ($n=6$). This confirms 5α-DHT pellet infusion was effective at inducing hair loss.

Figure 13:
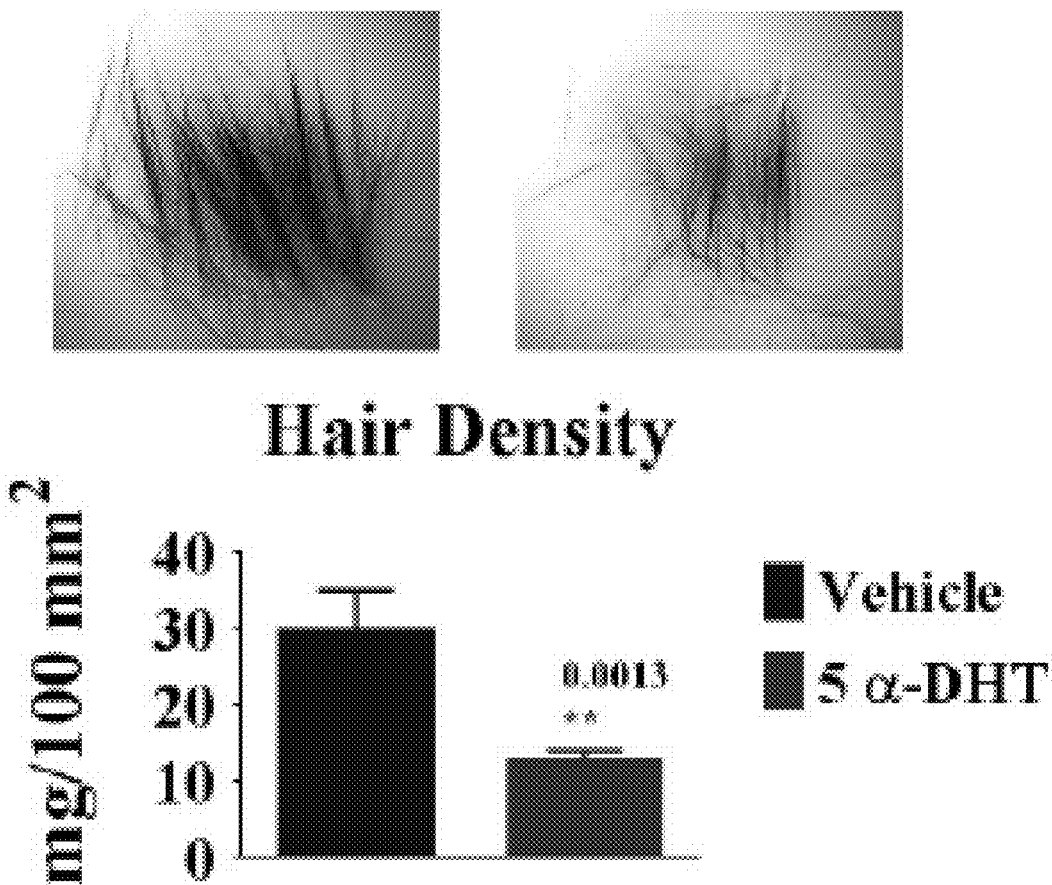
FIG. 13 shows the pattern hair baldness is induced in castrated male mice treated with 5α-DHT.
Figure 14A:
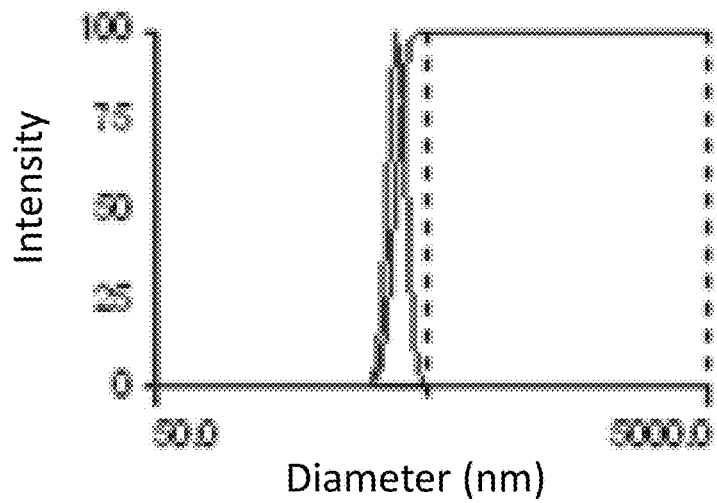
FIGS. 14A-14D show data from intensity dynamic light scattering size measurement and zeta potential of a 15× dilution of example formulations
Figure 14B:
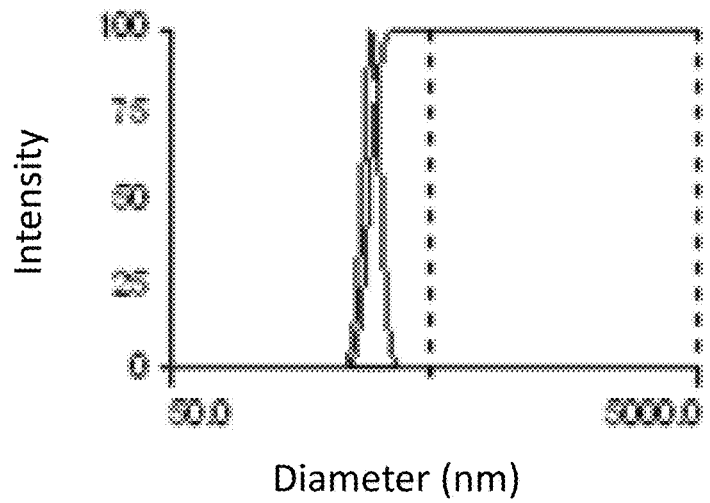
Figure 14C:
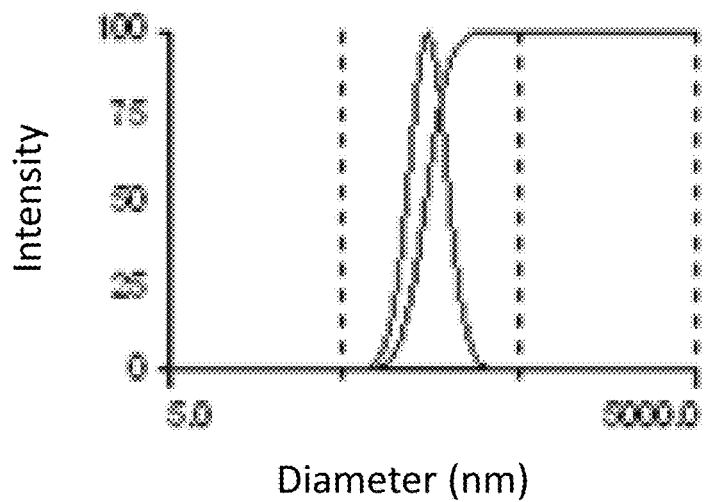
Figure 14D:
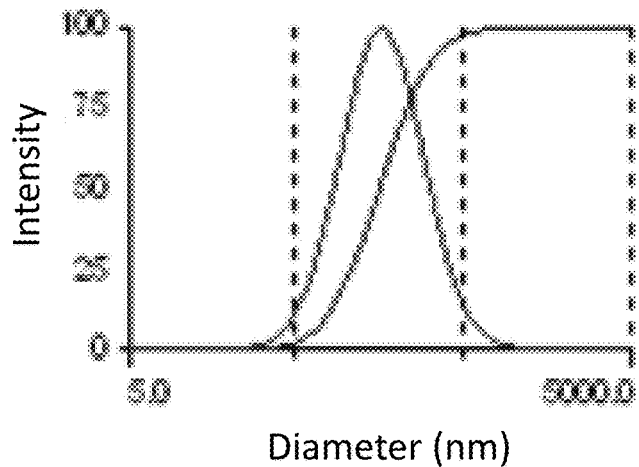

A second method was then used to directly quantitate hair density, hair quality and vellus hair occurrence. Specifically, mice were sacrificed and the pelts removed and fixed in buffered formalin for histology. Also, a plastic template with a fixed portal was used to demarcate a defined and identical region of interest (ROI) between the ears and above the shoulder blades (FIG. 12). Hair was then plucked from this region weighed and microscopically analyzed. Mice treated with 5α-DHT showed significantly reduced hair density, size and quality compared to placebo or control mice (FIG. 13). Detailed histological analysis of paraffin embedded sections are ongoing and will be reported later. FIG. 13 shows the pattern hair baldness is induced in castrated male mice treated with 5α-DHT. A plastic template with portal removed was used to facilitate hair removal from defined region of interest (ROI). Top pictures comparing control (right) and experimental (left) hairs removed from the ROI. Note smaller size and vellus like quality of the treated mice hair; and the bottom graph shows hair density (mg/100 mm$^2$) of vehicle treated and 5α-DHT treated mice. Hair density is significantly less with the 5α-DHT treated mice. The numbers shown on the histograms above the asterisk (*) is the p value calculated using a two-tailed unpaired t test at 95% confidence intervals. A $P<0.05$ is considered significant.

The peptide can be encapsulated in a delivery composition, such as a liposome or micro emulsion or nano emulsion. The encapsulation efficiency can be 44.3% to 79.8% to 87.7% in the composition as per experimental data. As such, the encapsulation efficiency can range from about 40% to about 90% or possibly higher. The composition can be prepared as described herein. In any event, a micro emulsion or nano emulsion can be loaded with the peptide at these efficiencies.

FIGS. 14A-14D shows data from intensity dynamic light scattering size measurement and zeta potential of a 15× dilution of four example formulations. Thus, the particles (e.g., liposomes) having the peptide can have a size or size distribution as per FIGS. 14A-14D. The median diameter can be about 382.2 or 295.4 or 152.8 or 166.1 nm, or +/−1%, 2%, 5%, 10%, or 20% thereof. The mean diameter can be as presented in these figures. The particle size range can also be up to about 430 nm or as small as about 66.1 nm.

One skilled in the art will appreciate that, for this and other processes and methods disclosed herein, the functions performed in the processes and methods may be implemented in differing order. Furthermore, the outlined steps and operations are only provided as examples, and some of the steps and operations may be optional, combined into fewer steps and operations, or expanded into additional steps and operations without detracting from the essence of the disclosed embodiments.

The present disclosure is not to be limited in terms of the particular embodiments described in this application, which are intended as illustrations of various aspects. Many modifications and variations can be made without departing from its spirit and scope, as will be apparent to those skilled in the art. Functionally equivalent methods and apparatuses within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is to be understood that this disclosure is not limited to particular methods, reagents, compounds compositions or biological systems, which can, of course, vary. It is also to be understood that the terminology used herein is for the purpose of describing particular embodiments only, and is not intended to be limiting.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should be interpreted to mean "at least one" or "one or more"); the same holds true for the use of definite articles used to introduce claim recitations. In addition, even if a specific number of an introduced claim recitation is explicitly recited, those skilled in the art will recognize that such recitation should be interpreted to mean at least the recited number (e.g., the bare recitation of "two recitations," without other modifiers, means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, such as in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," and the like include the number recited and refer to ranges which can be subsequently broken down into subranges as discussed above. Finally, as will be understood by one skilled in the art, a range includes each individual member. Thus, for example, a group having 1-3 cells refers to groups having 1, 2, or 3 cells. Similarly, a group having 1-5 cells refers to groups having 1, 2, 3, 4, or 5 cells, and so forth.

From the foregoing, it will be appreciated that various embodiments of the present disclosure have been described herein for purposes of illustration, and that various modifications may be made without departing from the scope and spirit of the present disclosure. Accordingly, the various embodiments disclosed herein are not intended to be limiting, with the true scope and spirit being indicated by the following claims. All references recited herein are incorporated herein by specific reference in their entirety: U.S. Ser. No. 11/521,684; and U.S. Pat. No. 7,825,217.

REFERENCES

David V, Martin A C, Hedge A M, Drezner M K, Rowe P S. ASARM peptides: PHEX-dependent & independent regulation of serum phosphate. Am J Physiol Renal Physiol. 2011; 300(3):F783-91.

Atkins G J, Rowe P S, Lim H P, Welldon K J, Ormsby R, Wijenayaka A R, Zelenchuk L, Evdokiou A, Findlay D M. Sclerostin is a locally acting regulator of late-osteoblast/pre-osteocyte differentiation and regulates mineralization through a MEPE-ASARM dependent mechanism. J Bone Miner Res. 2011; 26(7):1425-36.

Martin A, David V, Laurence J S, Schwarz P M, Lafer E M, Hedge A M, Rowe P S. Degradation of MEPE, DMP1, and release of SIBLING ASARM-peptides (minhibins): ASARM-peptide(s) are directly responsible for defective mineralization in HYP. Endocrinology. 2008; 149(4):1757-72.

David V, Martin A, Hedge A M, Rowe P S. Matrix extracellular phosphoglycoprotein (MEPE) is a new bone renal hormone and vascularization modulator. Endocrinology. 2009; 150(9):4012-23.

Rowe P S, Matsumoto N, Jo O D, Shih R N, Oconnor J, Roudier M P, Bain S, Liu S, Harrison J, Yanagawa N. Correction of the mineralization defect in hyp mice treated with protease inhibitors CA074 and pepstatin. Bone. 2006; 39(4):773-86.

Rowe P S N, Garrett I R, Schwarz P M, Carnes D L, Lafer E M, Mundy G R, Gutierrez G E. Surface Plasmon Resonance (SPR) confirms MEPE binds to PHEX via the MEPE-ASARM-motif: A model for impaired mineralization in X-linked rickets (HYP). Bone. 2005; 36(1):33-46.

Rowe P S, Kumagai Y, Gutierrez G, Garrett I R, Blacher R, Rosen D, Cundy J, Nawab S, Chen D, Drezner M K, Quarles L D, Mundy G R. MEPE has the properties of an osteoblastic phosphatonin and minhibin. Bone. 2004; 34(2):303-19. PMCID: 3357088.

Yuan B, Takaiwa M, Clemens T L, Feng J Q, Kumar R, Rowe P S, Xie Y, Drezner M K. Aberrant Phex function in osteoblasts and osteocytes alone underlies murine X-linked hypophosphatemia. J Clin Invest. 2008; 118(2):722-34.

Bresler D, Bruder J, Mohnike K L, Fraser D, Rowe P S N. Serum MEPE-ASARM-peptides are elevated in X-linked rickets (HYP): implications for phosphaturia and rickets. J Endocrinol. 2004; 183:R1-9.

Pfaffl M W. A new mathematical model for relative quantification in real-time RT-PCR. Nucleic Acids Res. 2001; 29(9):e45. PMCID: 55695.

Gluhak-Heinrich J, Ye L, Bonewald L F, Feng J Q, MacDougall M, Harris S E, Pavlin D. Mechanical loading stimulates dentin matrix protein 1 (DMP1) expression in osteocytes in vivo. J Bone Miner Res. 2003; 18(5):807-17.

Verma D D, Fahr A. Synergistic penetration enhancement effect of ethanol and phospholipids on the topical delivery of cyclosporin A. Journal of controlled release: official journal of the Controlled Release Society. 2004; 97(1): 55-66.

Crabtree J S, Kilbourne E J, Peano B J, Chippari S, Kenney T, McNally C, Wang W, Harris H A, Winneker R C, Nagpal S, Thompson C C 2010 A mouse model of androgenetic alopecia. Endocrinology 151(5):2373-80.

Park H J, Zhang N, Park D K 2011 Topical application of *Polygonum multiflorum* extract induces hair growth of resting hair follicles through upregulating Shh and beta-catenin expression in C57BL/6 mice. J Ethnopharmacol 135(2):369-75.

Park W S, Lee C H, Lee B G, Chang I S 2003 The extract of Thujae *occidentalis* semen inhibited 5alphareductase and androchronogenetic alopecia of B6CBAF1/j hybrid mouse. J Dermatol Sci 31(2):91-8.

Matias J R, Malloy V, Orentreich N 1989 Animal models of androgen-dependent disorders of the pilosebaceous apparatus. 1. The androchronogenetic alopecia (AGA) mouse as a model for malepattern baldness. Arch Dermatol Res 281(4):247-53.

Matias J R, Orentreich N 1988 The effect of testosterone, cyproterone acetate, and minoxidil on hair loss in the androchronogenetic alopecia mouse. Clin Dermatol 6(4): 169-76.

The invention claimed is:

1. A method of promoting hair growth, the method comprising:
    providing a polypeptide having a sequence that has at least 75% complementarity to or at least 75% identical to SPR4, wherein SPR4 is: TVNAFYSASTNYPRSLSYGAIGVIVGHEFTHGFDNNGRGENIADNG (SEQ ID NO: 21); and
    topically administering the polypeptide to a subject.

2. The method of claim 1, comprising providing a composition having a pharmaceutical carrier configured for topical application to a subject having the polypeptide; and administering the composition topically so as to administer the polypeptide to the subject.

3. The method of claim 1, comprising administering the polypeptide to:
    skin of the subject;
    a hair follicle of the subject; or
    a bald spot of the subject.

4. The method of claim 1, comprising administering the polypeptide so as to:
    modulate the Wnt/beta-catenin canonical pathway;
    regulate one or more genes involved in hair growth;
    accelerate hair growth;
    lengthen the anagen phase;
    reduce 5-alpha-reductase;
    suppress sclerostin; and/or
    increase active beta-catenin.

5. The method of claim 1, comprising administering the polypeptide in an amount to:
    treat alopecia and/or related syndromes;
    lengthen the anagen phase;
    increase hair growth on a bald spot; and/or
    increase hair follicle growth.

6. The method of claim 1, comprising administering the polypeptide in an amount to increase hair growth compared to when the polypeptide is not administered.

7. The method of claim 1, comprising administering the polypeptide by micro-needle injection.

8. The method of claim 7, wherein the micro-needle injection is performed by a derma-roller.

9. The method of claim 7, wherein the skin is not visibly damaged by the micro-needle injection.

10. The method of claim 7, comprising forming micro-pores in the skin with the micro-needle, and allowing the micro-pores to close after the micro-needle injection.

11. The method of claim 2, wherein the pharmaceutical carrier is a liposome.

12. The method of claim 1, wherein the polypeptide is included in a fusion polypeptide with a second polypeptide, wherein the second polypeptide includes an endosomal disrupting polypeptide.

13. The method of claim 2, wherein the SPR4 is dissolved in the pharmaceutical carrier selected from one or more of cetearyl alcohol, cetearyl glucoside, squalane, isopropyl palmate, octyldodecaonol, phenoxyethanol, methylparaben, etheylparaben, butylparaben, propylparaben, isobutylparaben, glycerin, butylene glycol, sodium acrylate, acryloyldimethyl taurate, isohexadecane, polysorbate, glyceryl stearate, dicaprylyl ether, alkyl benzoate, isononyl isononanoate, methylpropanediol, iodoproynyl butylcarbamate, triethanolamine, ketoconazole, serenoa serrulata extract, emu oil, niacin vitamin B3, caffeine, pyridoxine, L-pathenol, linolenic acid, simmondsia chinesis seed oil, zinc oxide, lecithin, ZnCb, L-a-phosphatidylcholine, ethanol, PBS, phospholipids, fatty acids, tocopherol, and derivatives thereof and equivalents thereof.

14. The method of claim 1, further comprising administering an active hair growth agent selected from minoxidil and finasteride.

15. The method of claim 2, wherein the pharmaceutical carrier is a micro emulsion or a nano emulsion.

16. The method of claim 2, wherein the pharmaceutical carrier contains $ZnCl_2$.

17. The method of claim 2, wherein the SPR4 is present at about 41% w/w in the composition, which is configured for topical delivery.

18. The method of claim 2, wherein the SPR4 is present at about 0.98-1 mg/ml in the topical composition.

19. The method of claim 2, wherein the carrier includes about 50 mg/ml to about 104 mg/ml lipid.

20. The method of claim 2, wherein the pharmaceutical carrier includes a lipid and ethanol.

* * * * *